US009944935B2

(12) United States Patent
Parks et al.

(10) Patent No.: US 9,944,935 B2
(45) Date of Patent: *Apr. 17, 2018

(54) METHODS TO IMPROVE VECTOR EXPRESSION AND GENETIC STABILITY

(71) Applicant: International AIDS Vaccine Initiative, New York, NY (US)

(72) Inventors: Christopher L. Parks, Boonton, NJ (US); Kevin J. Wright, Brooklyn, NY (US); Maoli Yuan, Brooklyn, NY (US); Christy K. Jurgens, Rahway, NJ (US); Xinsheng Zhang, Merrick, NY (US); Arban Domi, Parsippany, NJ (US); Simon Hoffenberg, Hartsdale, NY (US); Maria J. Chiuchiolo, Brooklyn, NY (US); Svetlana Rabinovich, Staten Island, NY (US); Aaron J. Wilson, Brooklyn, NY (US); Ivo C. Lorenz, Brooklyn, NY (US)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,260

(22) Filed: Apr. 20, 2016

(65) Prior Publication Data

US 2016/0222392 A1 Aug. 4, 2016

Related U.S. Application Data

(62) Division of application No. 13/792,103, filed on Mar. 10, 2013, now Pat. No. 9,347,065.

(60) Provisional application No. 61/617,368, filed on Mar. 29, 2012.

(51) Int. Cl.
| | |
|---|---|
| *C12N 15/67* | (2006.01) |
| *C12N 15/68* | (2006.01) |
| *C07K 14/005* | (2006.01) |
| *A61K 39/12* | (2006.01) |
| *C12N 7/00* | (2006.01) |
| *C12N 15/86* | (2006.01) |
| *C12N 15/64* | (2006.01) |
| *C12P 21/02* | (2006.01) |
| *A61K 39/21* | (2006.01) |
| *A61K 39/00* | (2006.01) |

(52) U.S. Cl.
CPC .............. *C12N 15/68* (2013.01); *A61K 39/12* (2013.01); *C07K 14/005* (2013.01); *C12N 7/00* (2013.01); *C12N 15/67* (2013.01); *C12N 15/86* (2013.01); *A61K 39/21* (2013.01); *A61K 2039/5254* (2013.01); *A61K 2039/5256* (2013.01); *C12N 2740/16122* (2013.01); *C12N 2740/16134* (2013.01); *C12N 2760/16034* (2013.01); *C12N 2760/18443* (2013.01); *C12N 2760/20243* (2013.01)

(58) Field of Classification Search
None
See application file for complete search history.

(56) References Cited

U.S. PATENT DOCUMENTS

| | | | |
|---|---|---|---|
| 9,347,065 B2 * | 5/2016 | Parks .................. | C07K 14/005 |
| 2010/0215691 A1 | 8/2010 | Parks et al. | |

FOREIGN PATENT DOCUMENTS

| | | |
|---|---|---|
| WO | 2005/098009 | 10/2005 |
| WO | 2009/148616 | 12/2009 |

OTHER PUBLICATIONS

Letourneau et al., "Design and Pre-Clinical Evaluation of a Universal HIV-1 Vaccine" 10 PLoS ONE e984 1-11 (2007).*
Humes et al., "Adaptation of Subtype A Human Immunodeficiency Virus Type I Envelope to Pig-Tailed Macaque Cells" 85(9) Journal of Virology 4409-4420 (Feb. 16, 2011).*
Allgaier, et al., "Vaccine production in Neurospora crassa" Biologicals, Jun. 2009, 37(3):128-132.
Berg, et. al., "HPV16 L1 capsid protein expressed from viable adenovirus recombinants elicits neutralizing antibody in mice" Vaccine, Apr. 2007, 25(17):3501-3510.
Clark, et al. "Recombinant vesicular stomatitis virus as an HIV-1 vaccine vector" Springer Seminars in Immunology, 2006, 28(3):239-253.
Entelechon, "Gene Optimization," http://www.entelechon.com/2008/09/gene-optimization/, Sep. 2008.
Kalwy, et al., "Toward more efficient protein" Molecular Biotechnology, Oct. 2006, 34(2):151-156, Oct. 2006.
Parks, et al. "Expression of a foreign gene by recombinant canine distemper virus recovered from cloned DNAs" Virus Research, 2002, 83:131-147.
Rabinovich, et al. "A Novel, Live-Attenuated Vesicular Stomatitis Virus Vector Displaying Conformationally Intact, Functional HIV-1 Envelope Trimers That Elicits Potent Cellular and Humoral Responses in Mice" PLOS ONE, Sep. 2014, 9(9):e106597.

Samudzi, et al., "Bacterial expression of Crimean-Congo hemorrhagic fever virus nucleoprotein and its evaluation as a diagnostic reagent in an indirect ELISA" Journal of Virological Methods, Sep. 2011, 179(1):70-76.

Wang, et. al., "Relative contributions of codon usage, promoter efficiency and leader sequence to the antigen expression and immunogenicity of HIV-1 Env DNA vaccine" Vaccine, May 2006, 24(21):4531-4540.

(Continued)

*Primary Examiner* — Nancy J Leith

(74) *Attorney, Agent, or Firm* — Vedder Price P.C.; Thomas J. Kowalski; Deborah L. Lu

(57) ABSTRACT

The present invention relates to methods of developing gene inserts that are more compatible with the host vectors by modifying a protein sequence to lessen potential interference with vector propagation while ensuring that the protein is expressed and processed efficiently and maintains desired structural features, and designing a gene with a nucleotide sequence that resembles the base composition of the host vector genome.

11 Claims, 16 Drawing Sheets
(11 of 16 Drawing Sheet(s) Filed in Color)

(56) References Cited

OTHER PUBLICATIONS

Whelan, et al. "The 5' Terminal Trailer Region of Vesicular Stomatitis Virus Contains a Position-Dependent cis-Acting Signal for Assembly of RNA into Infectious Particles" Journal of Virology, 1999, 73(1):307-315.

Williams, et. al., "Plasmid DNA vaccine vector design: Impact on efficacy, safety and upstream production" Biotechnology Advances, Jul. 2009, 27(4):353-370.

Zhang, et al., "Development of chimeric HIV Env immunogens for mucosal delivery with attenuated canine distemper virus (CDV) vaccine vectors," Retrovirology, Sep. 2012, 9(13):298.

* cited by examiner

CD5    Env Subtype B    VSV G

FIG. 7A
FIG. 7B
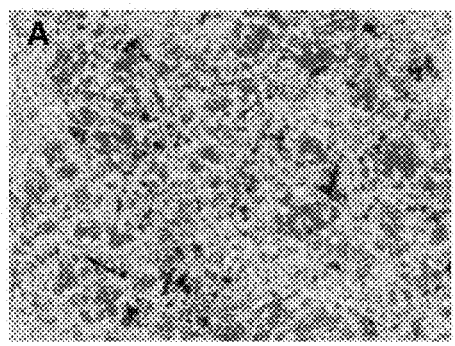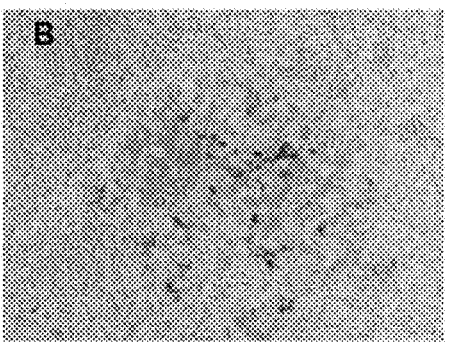

FIG. 8A   A.   3' | N | P | M | F | H | L | 5'

FIG. 8B   B.   | HIVCON | N | P | M | F | H | L |

FIG. 8C   C.   | N | P | HIVCON | S | M | F | H | L |

FIG. 8D   D.   | N | P | HIVCON | S | M | F | H | L |

FIG. 13

SEQUENCE LISTING

<160> NUMBER OF SEQ ID NOS: 7

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aggagccacc atg                                                        13

<210> SEQ ID NO 2
<211> LENGTH: 18
<212> TYPE: PRT
<213> ORGANISM: Thosea asigna virus

<400> SEQUENCE: 2

Glu Gly Arg Gly Ser Leu Leu Thr Cys Gly Asp Val Glu Glu Asn Pro
1               5                   10                  15

Gly Pro

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Lys Cys Leu Leu Tyr Leu Ala Phe Leu Phe Ile Gly Val Asn Cys
1               5                   10                  15

Lys

<210> SEQ ID NO 4
<211> LENGTH: 2325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ttcgaacaac taatatcctg tcttctctat ccctatgaaa aaaactaaca gagatcgatc    60
tgtttccttg acaccaggag ccaccatgaa gtgccttttg tacttagctt ttttattcat   120
cggggtgaat tgcaaggcta gcgcagagaa tttgtgggta acagtctact atggagtccc   180
tgtatggaag gatgcagaga caacattgtt ctgtgctagt gacgcaaagg cttacgagac   240
ggagaagcac aatgtgtggg caactcacgc atgtgtccca accgatccaa atcctcaaga   300
gattcatcta gagaatgtga ctgaagaatt caatatgtgg aagaataata tggtagagca   360
aatgcataca gatatcatta gtttatggga ccagtcactt aaaccctgcg ttaaattgac   420
gcctctatgt gtgacacttc aatgtactaa tgttacaaac aacataacag atgatatgag   480
aggagaactg aagaactgta gtttcaacat gacgacagag ttgcgtgaca gaaacagaa    540 agtgtattca ctattctatc ggttggatgt agtacagata aatgagaatc aaggaaacag   600
gtccaacaac tctaacaaag agtacagact tattaattgc aataccagtg ctatcacgca   660
agcctgccca aaggtttcat ttgaaccaat acctattcat tattgtgcac ctgctggatt   720

```
cgccatcctc aaatgtaaag acaagaagtt caatggaaca ggaccctgcc catcagtttc      780
aaccgttcag tgcacccacg gaatcaagcc tgtagttagt actcaattat tgttaaatgg      840
gagcttagct gaagaagaag ttatgattag atcagagaat attaccaata atgcgaagaa      900
catcttggtt caattcaata ctccagtcca gatcaattgc acaaggccta ataataatac      960
cagaaagagt ataagaattg gccaggaca ggcattctat gcaacaggag atataatcgg      1020
agacattcga caagcgcact gcactgtttc taaggccact tggaatgaaa cattgggtaa      1080
agttgtaaag caacttcgga agcatttcgg aaataacaca attattagat ttgcgaactc      1140
atctggaggg gatctggaag tgacaacaca ctctttcaat tgcggtggcg agttcttcta      1200
ttgtaataca agtggattat taactctac ttggatttca aatacctcag tccaaggatc       1260
taattcaaca gggtctaacg attctataac attccttgc cgtataaagc aaattattaa       1320
tatgtggcaa agaatcgggc aagcgatgta tgctccacct attcaaggcg tgattcgttg      1380
cgtttcaaac ataacagggt tgatcctgac cagggatgga ggctctacca attccaccac      1440
cgagaccttc cgtcccggtg gcggagatat gcggataaac tggagatcag agctctataa     1500
gtataaggtt gtgaagattg aacctcttgg agttgcccct acaagagcaa agagaagggt     1560
ggttggccga gagaagagag cagttggcat cggtgctgtc tttctcggat tcttggagc      1620 agctggatcc actatgggag cagcatcaat gacactaaca gtgcaggcta gaaatttgct     1680
tagcggaatc gttcagcagc agagcaattt actaagagca attgaagcac agcaacatct     1740
cttaaagttg acggtgtggg gcattaaaca actacaagcg agagtgcttg ccgtcgaaag     1800
atatttgcga gaccaacagc tattgggtat ttggggttgt tctgggaaat taatttgcac     1860
aacaaatgtt ccatggaact cctcctggag taataggaat ttaagtgaga tatgggacaa     1920
catgacatgg ttgcagtggg acaaggaaat ctcaaattat acacagataa tctatggatt     1980
attagaagag tctcagaatc agcaagagaa gaatgaacag gatttgcttg cattggataa     2040
gtgggcttct ctatggaact ggttcgatat tagtaattgg ctctggtata ttaagagctc     2100
tattgcctct ttttctttta tcatagggtt aatcattgga ctattcttgg ttctccgagt     2160 tggtattat ctttgcatta aattaaagca caccaagaaa agacagattt atacagacat       2220
agagatgaac cgacttggaa agtaaagctc aaatcctgca caacagattc ttcatgtttg     2280
aaccaaatca acttgtgata tcatgctcaa agaggcctta attaa                     2325
```

<210> SEQ ID NO 5
<211> LENGTH: 2340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
ttcgaacaac taatatcctg tcttctctat ccctatgaaa aaaactaaca gagatcgatc      60
tgtttccttg acaccaggag ccaccatgcc aatgggatca ttgcaaccat ggcaacatt      120 gtatttgttg ggaatgttgg ttgcatcagt tttggcagca gggaatttat gggttactgt     180
atattacgga gttcctgttt ggaaagaagc caagaccaca ttattctgtg ctagtgacgc     240
taaggcttac gagaaagaag tgcataacgt tgggcaaca catgcgtgtg tacctaccga     300
cccaaatcct caagaaatgg tacttgaaaa tgtaaccgaa atttttaaca tgtgaagaa      360 tgatatggtt gaacagatgc atgaagatgt cattagccta tgggatcaat ctctaaagcc     420
```

```
atgtgtaaag ctcacgcctt tgtgtgttac tctcgaatgc agacaggtca acacgacaaa    480
tgcaacatct tcagttaatg taaccaacgg agaggaaatt aagaattgta gctttaatgc    540
taccactgaa attcgtgata agaagcaaaa ggtgtatgca ttattttacc gattggatat    600
tgtgcctttg gaagaagagc gaaagggcaa ctcttccaaa tacagattaa tcaactgcaa    660
cacaagcgcg attacgcaag cttgtccaaa agtcaccttc gaccccatcc caatccatta    720
ctgtgcacct gccggatacg caattcttaa atgtaataat aagactttta atggaacagg    780
cccatgtaat aatgtgtcta cagtacagtg tacccacggc atcaaaccgg ttgtttctac    840
acagttgctc ttaaatgggt cattggctga aggagagatt attattcggt ctgaaaacct    900
caccaataat gtaaagacta tcatcgttca cttgaacgaa tctgtggaga ttgtctgtac    960
tagaccaaat aataatacca gaaagtcaat tagaatagga cctggacaaa ctttctacgc   1020
cacgggcgat attattggga atattagaca agcatattgc aacattaaga agatgattg   1080 gataagaaca ttgcagcggg ttgggaagaa attggccgaa catttcccca gaagaataat   1140
caactttaca tcacctgcag gaggagattt agaaattaca acgcattcat ttaactgtag   1200 agggagttc ttctattgta atacatcttc cttgttcaat tctacctaca atcctaatga   1260
taccaatagt aattcatcct cgtcgaattc ttccctggat attacaattc catgtaggat   1320
caaacaaatc attaatatgt ggcaagaagt cggtagagcg atgtacgcac ctcccattga   1380
aggaaatatt acatgcaaga gcaatattac ggggcctgttg ctcgttcgag atggtggagt   1440
cgaatccaat gaaacagaga tcttccgtcc tggaggaggg gatatgagaa ataattggag   1500
atctgaactc tataaataca agtagtggaa aattaaacca ttagggatag caccgacggc   1560
agctaaaaga cgagtggtgg agcgggagaa gcgtgctgtt ggattgggag ccgtcatatt   1620
tgggtttctc ggagctgcag gatctacaat gggtgcggca tcgattacac ttacagtgca   1680
agcaaggcaa ttacttagtg gaatagttca acaacaatca aatctgctga agccattga   1740 ggcacaacag catctgctac aattgacagt gtggggaatc aaacaattac agactagagt   1800
tcttgcaatc gaaagatatt taaaggacca acaactcttg ggcatttggg gatgttcggg   1860
aaagcttata tgtacaacag cagtaccatg gaactcttct tggtccaaca atcacacga   1920 cgagatttgg ggtaatatga cctggatgca atgggataga gagatttcta attacacaaa   1980
taccatctat agattgcttg aagattctca aaatcagcaa gagcagaacg agaaagattt   2040
attagcactc gatagttggg agaatttgtg gaattggttt tcaattacca agtggctctg   2100
gtacataaag tcgtccatcg caagcttctt cttcataata ggtctcatta ttggactctt   2160
tcttgtcctg agagtcggaa tatatctatg tatcaagctc aaacatacaa agaagaggca   2220
gatctataca gatattgaaa tgaatcgatt agggaagtaa agctcaaatc ctgcacaaca   2280
gattcttcat gtttgaacca aatcaacttg tgatatcatg ctcaaagagg ccttaattaa   2340
```

<210> SEQ ID NO 6
<211> LENGTH: 2316
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
ttcgaacaac taatatcctg tcttctctat ccctatgaaa aaaactaaca gagatcgatc     60
tgtttccttg aggagccacc atgccaatgg gatcattgca accattggca acattgtatt    120
```

```
tgttgggaat gttggttgca tcagtgttgg cagttgagaa attgtgggtt acagtttatt    180
atggagttcc agtttggaaa gaagcaacaa caacattgtt ctgtgcatct gatgcaaagg    240
catatgatac agaagttcat aatgtttggg caacacatgc atgtgttcca actgatccaa    300
atccacaaga agttgtgttg gagaatgtta cagaacattt caatatgtgg aagaataata    360
tggttgaaca aatgcaagaa gatattattt cattgtggga tcaatcattg aaaccatgtg    420
ttaaattgac accattgtgt gttacattga attgtaaaga tgttaatgca acaaatacaa    480
caaatgattc agaaggaaca atggaaagag gagaaattaa gaattgttca tttaatatta    540
caacatcaat tagagatgaa gttcagaaag aatatgcatt gttctataaa ttggatgttg    600
ttccaattga taataataat acatcatata gattgatttc atgtgataca tcagttatta    660
cacaagcatg tccaaagatt tcatttgaac caattccaat tcattattgt gcaccagcag    720
gatttgcaat cttgaaatgt aatgataaga catttaatgg aaagggacca tgcaagaatg    780
tttcaacagt tcaatgtaca catgaattga ccagttgtt ttcaacacaa ttgttgttga    840
atggatcatt ggcagaagaa gaagttgtta ttagatcaga taatttcaca aataatgcaa    900
agacaattat tgttcaattg aaagaatcag ttgaaattaa ttgtacaaga ccaaataata    960
atacaagaaa gtcaattcat attggaccag gaagagcatt ctatacaaca ggagaaatta   1020
ttggagatat tagacaagca cattgtaata tttcaagagc taaatggaat gatacattga   1080
aacaaattgt tattaaattg agagaacaat ttgagaataa gacaattgtg tttaatcatt   1140
catctggagg agatccagaa attgttatgc attcatttaa ttgtggagga gaattcttct   1200
attgtaattc aacacaattg tttaattcaa catggaataa taatacagaa ggatcaaata   1260
atacagaagg aaatacaatt acattgccat gtagaattaa acaaattatt aatatgtggc   1320
aagaagttgg aaaggctatg tatgcaccac caattagagg acaaattaga tgttcatcaa   1380
atattactgg attgttgttg acaagagatg gaggaattaa tgagaatgga acagaaatct   1440
ttagaccagg aggaggagat atgagagata attggagatc agaattgtat aaatataaag   1500
ttgttaagat tgaaccattg ggagttgcac caactaaagc aaagagaaga gttgttcaaa   1560
gagagaagag agcagttgga attggagcag tgttcttggg attcttggga gcagcaggat   1620
caacaatggg agcagcatca atgacattga cagttcaagc aagattgttg ttgtcaggaa   1680
ttgttcaaca acagaataat ttgttgagag caattgaagc acaacaaaga atgttgcaat   1740
tgacagtttg gggaattaaa caattgcaag caagagtgtt ggcagttgaa agatatttgg   1800
gagatcaaca attgttggga atttggggat gttcaggaaa gttgatttgt acaacagcag   1860
ttccatggaa tgcatcatgg tcaaataaat cattggatag aatttggaat aatatgacat   1920
ggatggaatg ggaaagagaa attgataatt acatcagaa aatttataca ttgattgaag   1980
aatcacagaa tcaacaagag aagaatgaac aagaattgtt ggaattggat aaatgggcat   2040
cattgtggaa ttggttgat attactaaat ggttgtggta tattaaatca tcaattgcat   2100
cattcttctt tattattgga ttgattattg gattgttctt ggtgttgaga gttggaattt   2160
atttgtgtat taaattgaaa catacaaaga agagacaaat ttatacagat attgaaatga   2220
atagattggg aaagtgagct caaatcctgc acaacagatt cttcatgttt gaaccaaatc   2280
aacttgtgat atcatgctca aagaggcctt aattaa                             2316
```

<210> SEQ ID NO 7
<211> LENGTH: 2760
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gcttaatctg tagcgttgac taatctacta accggcgcaa aactgctttc actatcgctt      60
aaaagcaatt ataaaaaact taggacacaa gagcctaagt cctctcctaa aaaggagcca     120
ccatgaagtg tttgttgtat ttggcattct tattcatcgg agtgaattgt aaggaggaga     180
aagcattctc acctgaagtg atccctatgt tcacagcatt atctgaggga gctactcctc     240
aagatcttaa cacaatgctt aacacagtcg gaggacatca agcagcaatg caaatgttga     300
aagatacaat taacgaggaa gcagcagaat gggatagaat ctataagaga tggataatat     360
taggattgaa caagattgtt agaatgtatt ctcctgtgtc aatccttgat ataagacaag     420
gacctaaaga gcctttcaga gattacgtcg atagatttgc aagaaattgt agagcaccta     480
gaaagaaggg atgttggaaa tgtgggaaag aaggacatca aatgaaagat tgtactgaga     540
gacaagctaa cttcttggga aagatatggc cttcaagatg gaaacctaag atgataggag     600
gaataggagg attattaaaa gtcagacaat atgatcaaat attgattgaa atatgtggac     660
ataaagctat tggaacagtc ctagtgggtc aacacctgt caacatcatt ggtagaaatc      720
ttctcactca aatcggatgt acactcaatt tcccaatatc acctattgag accgtgcctg     780
tcaaattgaa acctggaatg gatggaccta agtcaaaaca atggccatta actgaggaga     840
agattaaagc actggtagaa atttgtacag agatggagaa agaaggaaag atttccaaga     900
ttggtcctga gaatccttat aatactcctg tctttgctat taagaagaag gatagtacca     960
aatggaggaa attagtcgat ttcagagaac ttaacaagag gactcaagac ttctggaag    1020
tgcaattggg aatcccacac cctgcaggat gaagaagaa gaagtctgtc actgtcctag    1080
atgtgggaga tgcatatttc agtgtcccac tggatgaagg tttcagaaag tatacagcat    1140
tcacaatccc ttccattaat aatgaaacac ctggaataag atatcaatat aatgtcttac    1200
ctcaagggtg gaaaggatct ccagcaatat tccaatcatc aatgacaaag atcttggagc    1260
cttttcagagc tcagaatcca gagatagtta tttaccaata catggatgat ttgtatgttg    1320
ggtcagatct cgagatcgga cagcacagga tggagaatag atggcaagta atgattgtct    1380
ggcaagtcga tagaatgaga ataagaacat ggaaatcctt ggtgaaacat caccttacag    1440
aggaggcaga actggaactg gcagagaata gggaaatatt gaaagatcca gtgcatggtg    1500
tctattcga tccttctaaa gatctgatag cagagatcca gtactggcaa gcaacatgga    1560
ttcctgagtg ggaattcgtc aacacacctc cattagtgaa actatggtac caattagaga    1620
agaatgtcac cgagaacttc aacatgtgga gaacgatat ggtagatcaa atgcacgaag    1680
atatcatctc cttgtgggat caatcactta accttgtgt taaattgaca ccttgggtac    1740
ctgctcataa agggatagga ggaaacgaac aagtggataa attggtgtcc caagggatca    1800
ggaaagtctt gttcctagat ggaattgata agctcaagc aaaggaaatt gtcgcaagct    1860
gtgataagtg tcaattaaag ggagaggcaa tgcacggaca agtcgattgt tcacctggta    1920
tttggcaact tgattgtaca catttggagg gtaaagttat tctagtagca gtacatgtcg    1980
cttctggtta tattgaggca gaagtgatac ctgctgagac aggacaggag accgcatact    2040
ttctacttaa gttagctatg aataaggagc tcaagaagat aataggacaa gttagagatc    2100
aagcagagca ccttaagaca gctgtccaaa tggcagtgtt tatacacaac tttaagagaa    2160
agggtggaat cggaggatat tccgcaggag agagaatctg gaaaggtcct gctaaattgt    2220
```

```
tatggaaagg agaaggagca gttgtaatac aagataattc tgatataaaa gtagtcccta    2280
gaaggaaagc taagattatt agagattatg ggaaacaaat ggcaggagct gattgtgtgt    2340
ttctaggagc agcaggatcc actatgggag ctgcatcaat gacacttacc gtgcaggcta    2400
gacagcttct ttcaggaatt gtacagcaac agaataattt gctaagagca attgaagctc    2460
aacaacactt acttcaactt acagtctggg gaatcaagca agcatgtaca ccttatgata    2520
tcaaccaaat gctgagagga ccaggaagag catttgtaac aatccctaat cctttattgg    2580
gtctggatga aggaagagga tcactgttga catgtggaga tgtcgaagag aatcctggac    2640
ctactgaggt gtacgacttc gatcagtcct cttgggacac caaaggctca ttggcccta    2700 ttttgcctac cacttatccc gatggtaggc tcataccca agtcagagta atagatccag    2760
```

METHODS TO IMPROVE VECTOR EXPRESSION AND GENETIC STABILITY

RELATED APPLICATIONS AND INCORPORATION BY REFERENCE

This application is a divisional of U.S. application Ser. No. 13/792,103 filed Mar. 10, 2013, which claims priority to U.S. provisional patent application Ser. No. 61/617,368 filed Mar. 29, 2012. Reference is made to U.S. patent application Ser. No. 12/708,940 filed Feb. 19, 2010 and U.S. provisional patent application Serial Nos. 61/537,497 filed Sep. 21, 2011; 61/552,240 filed Oct. 27, 2011 and 61/614,584 filed Mar. 23, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was supported, in part, by CAVD Grant ID: 38606, CAVD Grant ID: OPP1033117 and NIAID R01: 1R01AI084840-01. The federal government may have certain rights to this invention.

The instant application contains a Sequence Listing which has been submitted in ASCII format via EFS-Web and is hereby incorporated by reference in its entirety. Said ASCII copy, created on Mar. 20, 2013, is named 43094.01.2021_SL.txt and is 14,631 bytes in size.

FIELD OF THE INVENTION

The present invention relates to methods for tailoring gene insert designs to improve protein expression, vector propagation, and genetic stability in individual vector platforms

BACKGROUND OF THE INVENTION

Problems encountered frequently during vaccine delivery vector development include poor foreign protein expression, inefficient or incomplete post-translational processing of the immunogen, diminished vector propagation, and gene insert instability. These problems are often related to the foreign gene being nonessential for vector propagation and the negative effect on replicative fitness that often is conferred by the biological or physical characteristics of the nucleotide sequence or the encoded protein.

Earlier 'gene optimization' procedures used to develop gene inserts for vaccine vectors focused primarily on designing synthetic coding sequences with the characteristics of highly expressed cellular mRNAs (Andre et al. 1998. J Virol 72:1497-1503, Barouch 2006. The Journal of pathology 208:283-289, Donnelly et al. 1997. DNA vaccines. Annu Rev Immunol 15:617-648 and Haas et al. 1996. Codon usage limitation in the expression of HIV-1 envelope glycoprotein. Current biology: CB 6:315-324). Although this general optimization approach often increases expression of the encoded polypeptide, it also can result in a gene insert that is poorly compatible with the vector because the expressed protein is cytotoxic and/or the engineered nucleotide sequence is difficult to replicate and unstable. Accordingly, there is a need to develop a gene design approach that makes it possible to abundantly express foreign proteins while also reducing the negative effect caused by introducing foreign gene sequences into a vector genetic background.

Citation or identification of any document in this application is not an admission that such document is available as prior art to the present invention.

SUMMARY OF THE INVENTION

The present invention relates to methods for tailoring gene insert designs to improve protein expression, vector propagation, and genetic stability in individual vector platforms. Earlier gene 'optimization' procedures were primarily directed to improving expression in prokaryotic or eukaryotic cell substrates and organisms. The method described herein may be utilized to prepare foreign gene inserts that 1) closely resemble the nucleotide composition of the vector genetic background; 2) lack sequences that might cause insert instability during vector propagation; and, 3) lack sequences known to inhibit expression in eukaryotic cells.

To reduce the negative selective pressure caused by insertion of a foreign gene sequence while also maintaining abundant protein expression needed to develop an immunogenic vaccine, Applicants have developed a new strategy for designing protein-coding sequences for use in vaccine vectors. In summary, the objective of the method is to develop a gene insert that is more compatible with the host vector by 1) modifying the protein sequence to lessen potential interference with vector propagation while ensuring that the polypeptide is expressed and processed efficiently and maintains desired structural features, and 2) designing the gene with a nucleotide sequence that resembles the base composition of the host vector genome.

The objective is to develop a gene design approach that makes it possible to abundantly express foreign proteins while also reducing the negative effect caused by introducing foreign gene sequences into a vector genetic background. The gene optimization approach incorporates three elements:

1. The synthetic gene is designed with a codon bias similar to the vector sequence 2. Nucleotide sequence elements in the synthetic gene that resemble known 'hot spots' for mutation, inhibitors of replication or gene expression, or have the potential to direct inappropriate RNA processing are interrupted using synonymous codons.

3. Protein functional domains that modulate translation, post-translational processing, and cellular compartmentalization may be replaced with analogous operable elements from other polypeptides to produce an immunogen that is expressed abundantly while having less negative effect on vector propagation and fitness.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 2 illustrates protein domain swaps used to develop hybrid Env-VSV G proteins (EnvG) that are expressed abundantly but retain functional and antigenic properties of native Env. A) Schematic of VSV G; B) Native Env protein; C) EnvG protein containing the VSV G signal peptide and G cytoplasmic domain; D) Like the protein illustrated in C except that the precise points of fusion between the Env transmembrane domain and the G cytoplasmic domain differ and are as described by Johnson et al. (Virology 251:244-252); E) EnvG protein containing the VSV G signal peptide, G transmembrane domain, and G cytoplasmic domain; F-H) EnvG containing the VSV G signal peptide, varying lengths of the membrane-proximal extracellular stem domain from G, the G transmenbrane sequence, and the G cytoplasmic domain. The amino acid coordinates are provided in Table 1.

Figure 3B:
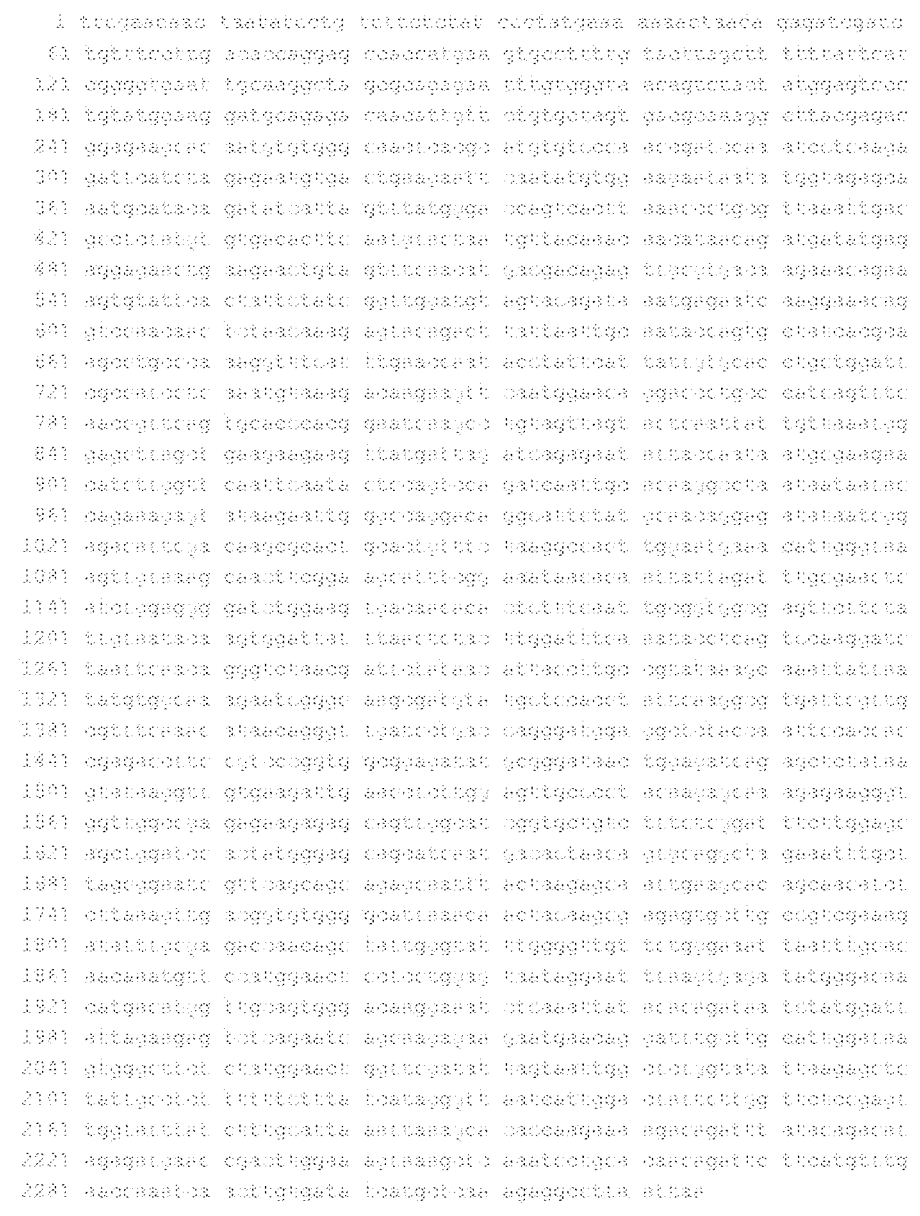

FIGS. 3A and 3B depict a Subtype A EnvG Immunogen. Part A is a schematic showing the protein domains incorporated into the EnvG immunogen. Part B is the corresponding nucleotide sequence (SEQ ID NO: 4) developed for VSV vectors.

Figure 4B:
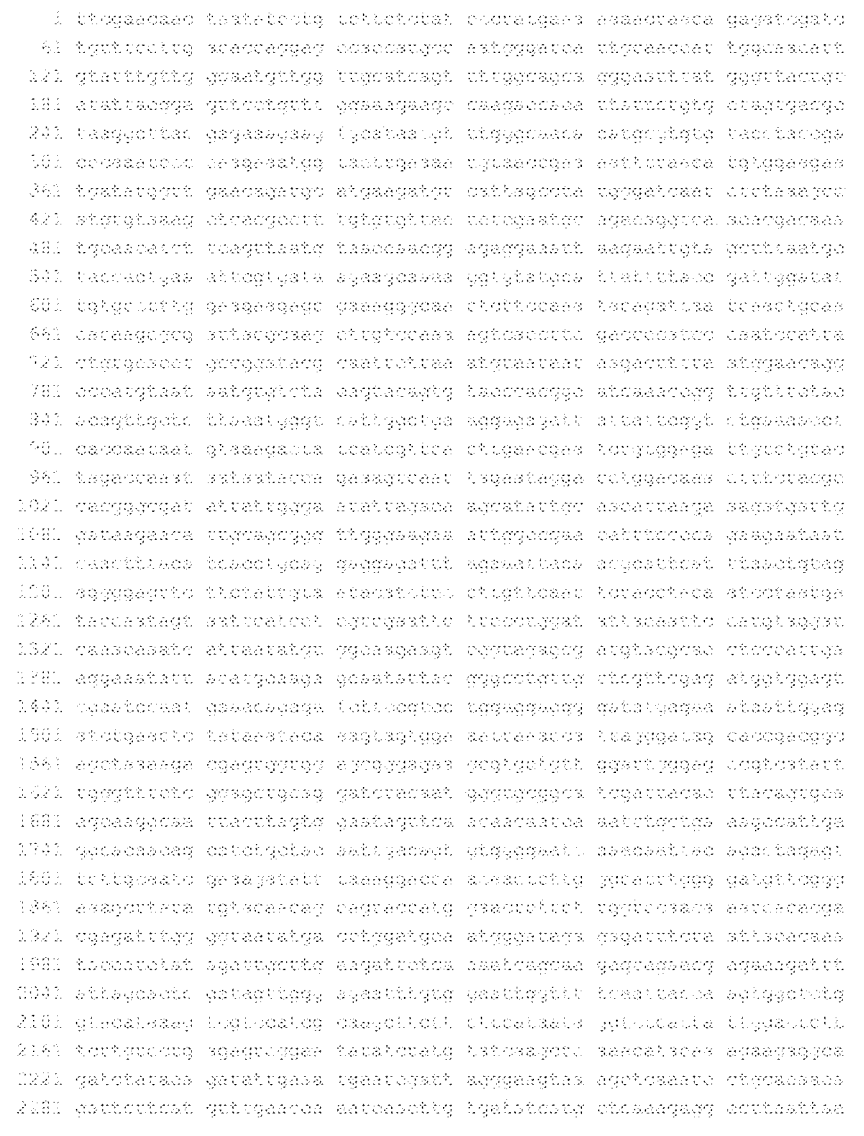

FIGS. 4A and 4B depict a Subtype C EnvG hybrid immunogen. Part A illustrates the domains incorporated in the polypeptide. The gene sequence is provided in Part B (SEQ ID NO: 5).

Figure 5A:
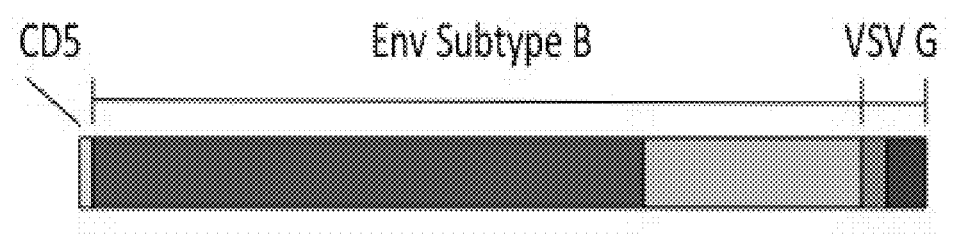
Figure 5B:
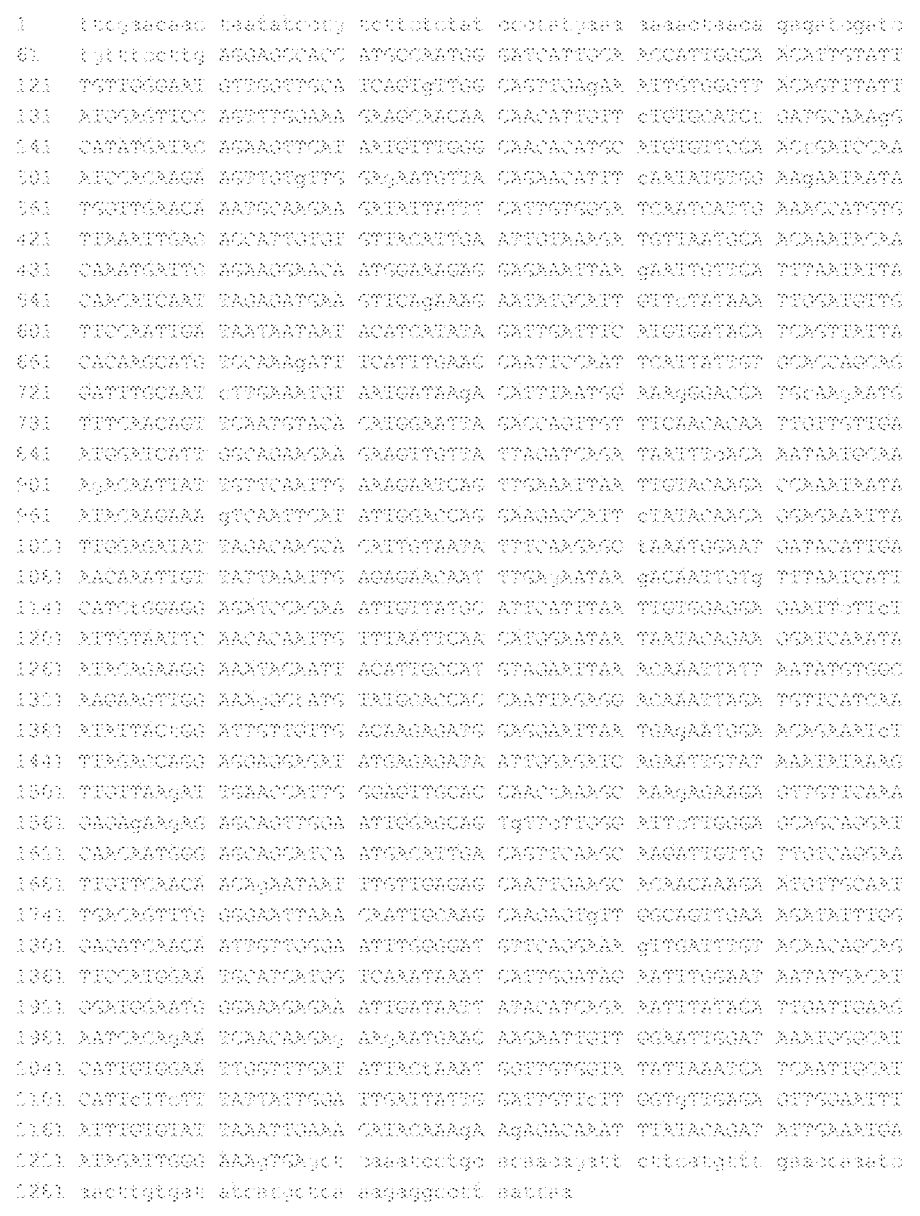

FIGS. 5A and 5B depict a Subtype B EnvG hybrid immunogen. Part A illustrates the domains incorporated in the polypeptide. The gene sequence is provided in Part B (SEQ ID NO: 6).

FIGS. 7A and 7B depict Vero cells infected with CDV-HIV Env vectors expressing (A) Subtype A or (B) Subtype C Env. The plaques were stained with monoclonal antibody 4E10, which is specific for sequences in the gp160 precusor or the gp41 subunit of Env (Zwick et al., J Virol 75:6692-6699).

FIGS. 8A-8D depict Canine distemper virus (CDV) vectors encoding the HIVCON Immunogen. The single-stranded, negative-sense, nonsegmented RNA genome of CDV (Part A) contains 6 genes. Transcription start and stop signals flank each gene. Three HIVCON genes have been prepared for incorporation into the CDV genome. Illustrated in Part B, a HIVCON insert has been designed with a codon bias similar to CDV with viral transcription start and stop signals flanking the synthetic gene. The HIVCON coding sequence represented in Part B was modified further for insertion downstream of the CDV P gene. The nucleotide sequence is provided below (FIG. 9). Notably, the HIVCON coding sequence was fused to the M (Matrix) gene of CDV to form a polycistronic coding sequence. The 2A-like element (Luke et al., J Gen Virol 89:1036-1042) inserted between the HIVCON and M coding sequence encodes a polypeptide cleavage element, which allows release of the HIVCON and M polypeptides from a larger fusion protein precursor. In Part D, the strategy described in Part C was used to insert the gene downstream of CDV P except that the HIVCON coding sequence was the same as described by Letourneau et al (PLoS ONE 2:e984). The VSV signal sequence was added to all HIVCON constructs.

FIG. 9 depicts a design of a HIVCON gene for expression from CDV vectors. An annotated nucleotide sequence (SEQ ID NO: 7) is provided for the gene design illustrated in FIG. 8C.

FIGS. 10A and 10B depict transient expression of EnvG immunogens by plasmid DNA vectors. A) Schematic of the EnvG gene, which was expressed by the plasmid used for transient expression. B) Analysis of transfected 293 cells with a panel of antibodies (Walker et al., Nature 477:466-470, Walker et al., Science 326:285-289, Zwick and Burton, Curr HIV Res 5:608-624) used to probe antigenic profiles.

FIG. 11 depicts designs of Hybrid Env-F proteins. The Subtype C Env gene was further modified to generate coding sequences for hybrid Env proteins that contain domains derived from CDV F.

FIG. 13 depicts four chimeric EnvF constructs (Subtype C, strain 16055) which were designed and cloned under CMV promoter in plasmid DNA vector (FIG. 11). In addition to coding sequence design described above, F domain substitutions were made as illustrated in FIG. 11.

DETAILED DESCRIPTION OF THE INVENTION

Figure 1:
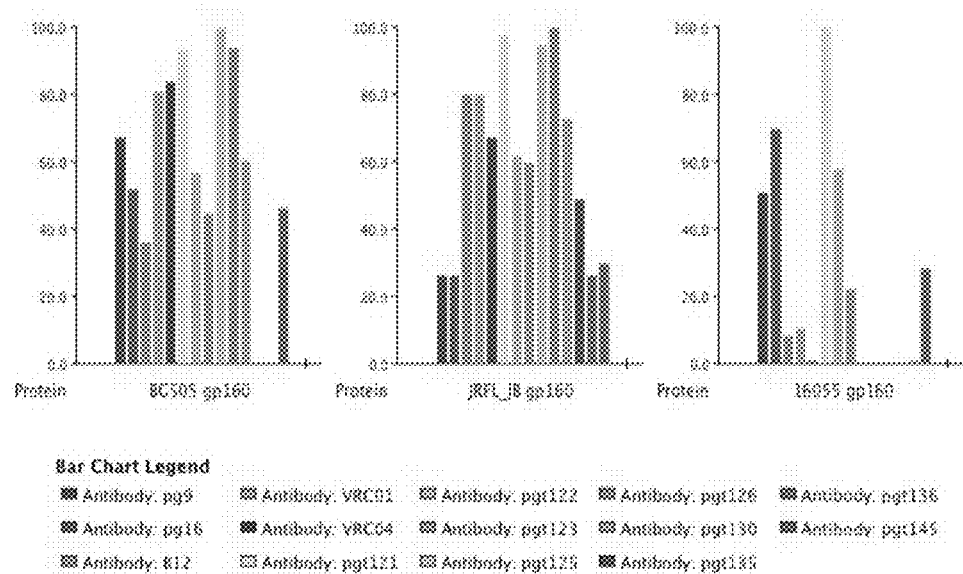
FIG. 1 depicts antibody-binding profiles for Env immunogens expressed on the cell surface. Env immunogens are expressed in cells transfected with plasmid vectors or infected with viral vectors and subsequently reacted with monoclonal antibodies that react with specific domains in HIV Env. Antibody binding is detected by cell sorting.
Figure 3A:
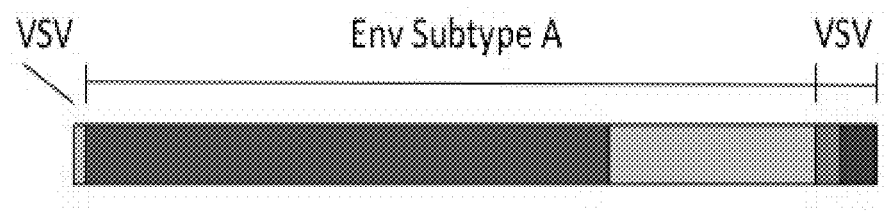
Figure 4A:
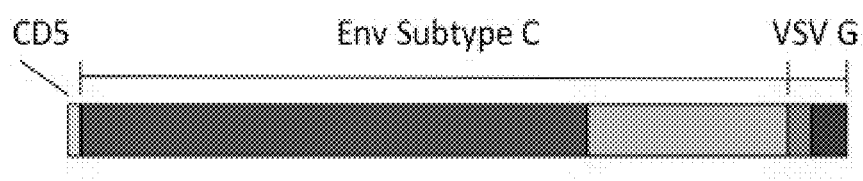

The present invention relates to methods for producing improved gene inserts for vaccine vectors. The strategy used for HIV immunogens may be applied to a broad range of other polypeptides including viral glycoproteins from respiratory syncytial virus, human parainfluenza virus, human cytomegalovirus, herpes simplex, and others.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:
  a. Fab, the fragment which contains a monovalent antigen-binding fragment of an antibody molecule can be produced by digestion of whole antibody with the enzyme papain to yield an intact light chain and a portion of one heavy chain;
  b. Fab', the fragment of an antibody molecule can be obtained by treating whole antibody with pepsin, followed by reduction, to yield an intact light chain and a portion of the heavy chain; two Fab' fragments are obtained per antibody molecule;
  c. F(ab')$_2$, the fragment of the antibody that can be obtained by treating whole antibody with the enzyme pepsin without subsequent reduction; F(ab')2 is a dimer of two Fab' fragments held together by two disulfide bonds;
  d. scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and IN sequences of the invention may be altered in these ways.

With respect to codon optimization, the nucleic acid molecules of the invention have a nucleotide sequence that encodes the antigens of the invention and can be designed to employ codons that are used in the genes of the subject in which the antigen is to be produced. Advantageously, codons are optimized using a bias that is specific for the viral vector and not for the host cell. Many viruses, including HIV and other lentiviruses, use a large number of rare codons and, by altering these codons to correspond to codons commonly used in the desired subject, enhanced expression of the antigens can be achieved. In another embodiment, the codons used may be "humanized" codons, i.e., the codons are those that appear frequently in highly expressed human genes (Andre et al., J. Virol. 72:1497-1503, 1998) instead of those codons that are frequently used by HIV. Such codon usage may provide for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993;Nature Genetics 3: 266-272; Karlin & Altschul, 1993;Proc. Natl. Acad. Sci. USA 90: 5873-5877; all of which are incorporated by reference herein).

The various recombinant nucleotide sequences and antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antigens of the present invention may be used in accordance with the present invention. In certain embodiments, the antigens and/or antibodies of the present invention may be used in vitro (such as using cell-free expression systems) and/or in cultured cells grown in vitro in order to produce the encoded antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antigens be expressed in vivo, any vector that allows for the expression of the antigens of the present invention and is safe for use in vivo may be used. In preferred embodiments the vectors used are safe for use in humans, mammals and/or laboratory animals.

For the antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antigens and/or antibodies of the invention can be expressed.

For example, when the aim is to express the antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoan vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antigens under the identified circumstances.

When the aim is to deliver antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antigens of the invention in a laboratory animal, such as for pre-clinical testing of the HIV-1 immunogenic compositions and vaccines of the invention. In other embodiments, it will be desirable to express the antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

The present invention relates to recombinant enveloped viruses as vectors, however, other vectors may be contemplated in other embodiments of the invention such as, but not limited to, prime boost administration which may comprise administration of a recombinant envelope virus vector in combination with another recombinant vector expressing one or more HIV epitopes.

VSV is a practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

The VSVs of U.S. Pat. Nos. 7,468,274; 7,419,829; 7,419,674; 7,344,838; 7,332,316; 7,329,807; 7,323,337; 7,259,015; 7,244,818; 7,226,786; 7,211,247; 7,202,079; 7,198,793; 7,198,784; 7,153,510; 7,070,994; 6,969,598; 6,958,226; RE38,824; PPI5,957; 6,890,735; 6,887,377; 6,867,326; 6,867,036; 6,858,205; 6,835,568; 6,830,892; 6,818,209; 5 6,790,641; 6,787,520; 6,743,620; 6,740,764; 6,740,635; 6,740,320; 6,682,907; 6,673,784; 6,673,572; 6,669,936; 6,653,103; 6,607,912; 6,558,923; 6,555,107; 6,533,855; 6,531,123; 6,506,604; 6,500,623; 6,497,873; 6,489,142; 6,410,316; 6,410,313; 6,365,713; 6,348,312; 6,326,487; 6,312,682; 6,303,331; 6,277,633; 6,207,455; 6,200,811; 6,190,650; 6,171,862; 6,143,290; 6,133,027; 6,121,434; 6,103,462; 6,069,134; 6,054,127; 6,034,073; 5,969,211; 10 5,935,822; 5,888,727; 5,883,081; 5,876,727; 5,858,740; 5,843,723; 5,834,256; 5,817,491; 5,792,604; 5,789,229; 5,773,003; 5,763,406; 5,760,184; 5,750,396; 5,739,018; 5,698,446; 5,686,279; 5,670,354; 5,540,923; 5,512,421; 5,090,194; 4,939,176; 4,738,846; 4,622,292; 4,556,556 and 4,396,628 may be contemplated by the present invention.

The CDVs of U.S. Pat. Nos. 7,879,336; 7,833,532; 7,378,101; 7,288,265; 6,673,572; 6,228,846; 5,843,456; 5,178,862 and 4,992,272 may be contemplated by the present invention.

The measles of U.S. Pat. Nos. 6,884,786; 5,578,448 and 4,016,252 may be contemplated by the present invention.

Other envelope viruses are also contemplated, such as a herpesvirus, poxvirus, hepadnavirus, flavivirus, togavirus, coronavirus, hepatitis D virus, orthomyxovirus, paramyxovirus, rhabdovirus, bunyavirus or a Filovirus.

Problems encountered frequently during vaccine delivery vector development include poor foreign protein expression, inefficient or incomplete post-translational processing of the immunogen, diminished vector propagation, and gene insert instability. These problems are often related to the foreign gene being nonessential for vector propagation and the negative effect on replicative fitness that often is conferred by the biological or physical characteristics of the nucleotide sequence or the encoded protein. To reduce the negative selective pressure caused by insertion of a foreign gene sequence while also maintaining abundant protein expression needed to develop an immunogenic vaccine, Applicants have developed a new strategy for designing protein-coding sequences for use in vaccine vectors. In summary, the objective of the method is to develop a gene insert that is more compatible with the host vector by 1) modifying the protein sequence to lessen potential interference with vector propagation while ensuring that the polypeptide is expressed and processed efficiently and maintains desired structural features, and 2) designing the gene with a nucleotide sequence that resembles the base composition of the host vector genome.

Earlier 'gene optimization' procedures used to develop gene inserts for vaccine vectors focused primarily on designing synthetic coding sequences with the characteristics of highly expressed cellular mRNAs. Although this general optimization approach often increases expression of the encoded polypeptide, it also can result in a gene insert that is poorly compatible with the vector because the expressed protein is cytotoxic and/or the engineered nucleotide sequence is difficult to replicate and unstable. Accordingly, Applicants' objective is to develop a gene design approach that makes it possible to abundantly express foreign proteins while also reducing the negative effect caused by introducing foreign gene sequences into a vector genetic background. Applicants' gene optimization approach incorporates three elements:

1. The synthetic gene is designed with a codon bias similar to the vector sequence
2. Nucleotide sequence elements in the synthetic gene that resemble known 'hot spots' for mutation, inhibitors of replication or gene expression, or have the potential to direct inappropriate RNA processing are interrupted using synonymous codons.
3. Protein functional domains that modulate translation, post-translational processing, and cellular compartmentalization can be replaced with analogous operable elements from other polypeptides to produce an immunogen that is expressed abundantly while having less negative effect on vector propagation and fitness.

Below, Applicants' gene design approach is illustrated with HIV Env genes designed specifically for expression by live vesicular stomatitis virus (VSV) vectors. Other examples follow to show that the strategy is not limited to VSV vectors or Env immunogens.

Development of a vaccine that will expose the immune system to a properly configured Env immunogen that is nearly identical to the functional structures found on the surface of HIV particles is a difficult technical problem, because the active form of Env is a membrane-bound, unstable, multi-subunit complex. Functional Env protein is part of trimeric glycoprotein spike that is assembled from subunits derived from a virus-encoded precursor protein (gp160). Maturation of gp160 involves extensive post-translational modification including glycosylation, formation of multiple intra-chain disulfide linkages, and proteolytic cleavage into two subunits, which include the smaller transmembrane glycoprotein gp41 and the soluble extracellular subunit gp120. Subunits gp41 and gp120 are held together by noncovalent interactions to form a monomer and three Env monomers associate into a complex to form the functional trimeric spikes found on surface of the HIV particles and infected cells. Design and production of a vaccine that can deliver natively configured trimeric spike immunogens must take into account: 1) synthesis of immunogens that are modified extensively and correctly; 2) assembly of a stable multisubunit complex held together by labile noncovalent interactions; 3) known insolubility of the native gp41 subunit; and 4) the native spike complex is naturally anchored to the lipid bilayer of cells and virus particles. These biochemical features make it difficult to produce a soluble protein immunogen that accurately mimics a trimeric spike; thus, a vector platform that will direct synthesis of the native Env spike following vaccine administration is a more practical approach.

The methods used before to improve Env expression are not applicable to all vectors and immunogen designs. For example, protein modifications introduced to improve expression might alter structural conformation producing unpredictable effects on important epitopes. Nucleotide sequence optimization also can have unpredictable effects. Notably, common gene optimization procedures generally use a codon bias reflecting highly expressed mammalian mRNAs, which may not be compatible with viral vectors that have genomes with much different nucleotide compositions. This can be illustrated with the HIV Env gene. Using online web tools to design an Env gene with a codon bias reflecting highly expressed mammalian genes results in a coding sequence that has a guanine plus cytosine (G+C) content of approximately 60%. Gene inserts with high G+C content like this might be poorly expressed or unstable when inserted into vectors like those based on RNA viruses such as measles virus, bovine parainfluenza virus, and vesicular stomatitis virus, which have noticeably lower genomic G+C content of 47%, 36%, and 42%, respectively.

Applicants' goal is to make genetically stable vaccine vectors that abundantly express trimeric membrane-bound Env spikes that closely mimic the structural properties of the functional glycoprotein complex found on HIV particles. To achieve this objective, Applicants have developed a strategy to design gene inserts that are tailored to the vector. To ensure that the modified Env immunogens encoded by Applicants' vectors are processed accurately and retain a native configuration, Applicants have developed a method to confirm the presence of different classes of epitopes known to bind with virus-neutralizing antibodies (FIG. 1). In cells expressing the Env immunogens, FACS analysis is used with antibody probes including monoclonal antibodies that recognize the CD4 binding site (VRC01 and b12), determinant formed by the V1/V2 loops (PG9 and PG16), structures formed by the glycosylated sequences in the V3 loop (PGT121, PGT126, PGT128, and PGT130), the membrane-proximal external region (2F5 and 4E10), and unique structures formed specifically by the trimeric spike (PGT145). The presence of epitopes is detected on the cell surface by FACs to confirm that the vector is directing expression of a correctly processed and assembled Env spike.

The foreign gene insert optimization strategy Applicants have developed may be illustrated using HIV Env (strain JR-FL, subtype B). Adaptation of this method to other types of gene inserts and vectors also includes EnvF fusions proteins for canine distemper virus (CDV) vectors; SIV genes for CDV; SIV genes for VSV; HIV Gag for VSV; HIVCON for CDV.

In summary, the major elements of the Env gene insert optimization strategy are:
1. Design of the Env gene insert using a nucleotide bias characteristic of the VSV genome
2. Removal of RNA sequence elements that might cause VSV genome instability, inhibit protein translation, reduce mRNA stability, or promote unwanted RNA processing.
3. Addition of cis-acting RNA sequences that promote efficient translation.
4. Design of a hybrid Env immunogen in which select Env functional domains are substituted with sequences from the VSV glycoprotein (G) to promote improved protein expression. Domains from G found to improve expression while retaining Env structures recognized by neutralizing antibodies include: a) the VSV G signal sequence (secretory signal); b) the membrane proximal extracellular stem domain; c) the transmembrane domain; and/or the intracellular cytoplasmic domain. It is important to note that in some instances, replacement of Env domains with sequences from G was not beneficial. For example, the VSV signal sequence did not enhance expression or genetic stability in some VSV vectors, but further investigation revealed that substitution of the signal sequence from the cellular CD5 protein was beneficial. Thus, the domain swap strategy is generally applicable, but requires some empirical determination to achieve the greatest benefit.

Nucleotide sequence design: of HIV-1 Env (subtype B, strain JR-FL) gene inserts for expression from VSV vectors includes:
1. The Optimizer Web Tool (Nucleic Acids Res 35:W126-131) was used to generate a new Env coding sequence with a codon bias similar to VSV.
2. The computer-generated sequence was then scanned for sequences that might have a negative effect on RNA transcription or stability, translation, or VSV genome replication. These sequences were removed by replacing nucleotides in the synthetic Env coding sequence with synonymous codons. Sequences targeted for substitution included:
   a. Most homopolymer stretches ≥5 nucleotides
   b. Sequences resembling cellular mRNA splicing signals identified using NNSPLICE webtool (J Comput Biol 4:311-323)
   c. Sequences resembling known RNA instability elements (Mol Cell Biol 15:2219-2230)
   d. Sequences resembling the known cleavage and polyadenylation signal (AAUAAA) (MMBR 63:405-445)

e. Sequences resembling transcription start and stop signal consensus for VSV (Biochim Biophys Acta 1577:337-353)
3. The 5' end of the coding sequences was modified to include a translation initiation context resembling a consensus for the other VSV genes (GTCATCATG)
4. Stop codon context was modified to resemble highly-expressed human genes according to Kochetov (FEBS letters 440:351-355)
5. 5' end includes a HindIII site for cloning into the rVSV genomic cDNA.
6. For molecular cloning purposes, two sequences were edited to remove HindIII sites in the coding sequence.
7. 3' end was modified by addition of a BamHI site for cloning into the rVSV genomic cDNA Protein Modifications. Multiple domain swaps were tested identifying several that 1) improve Env expression; 2) retain functional properties of native Env; and 3) preserve critical structural determinants recognized by neutralizing antibodies.

TABLE 1

Figure 2:
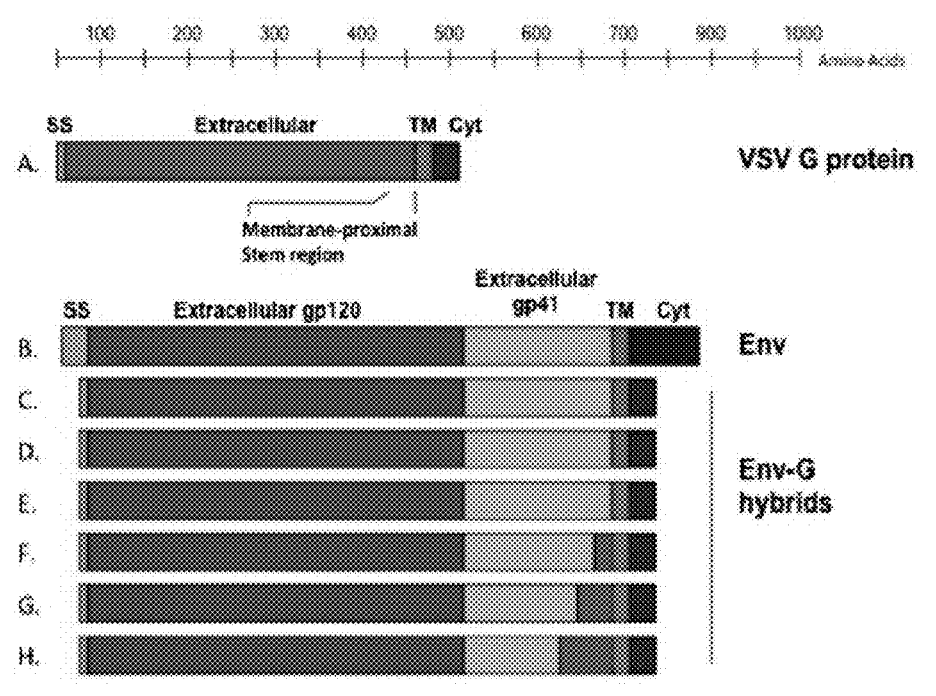

Amino acid coordinates for sequences of HIV Env and VSV G incorporated into EnvG hybrids illustrated in FIG. 2.

| Protein | Name | N-Terminal Signal Peptide | Env (JR-FL) | VSV G |
|---------|------|---------------------------|-------------|-------|
| A | VSV G | 1-17 VSV G | None | 18-511 |
| B | Env (JR-FL) | 1-29 Env | 30-847 | None |
| C | EnvG-CT | 1-17 VSV | 30-695 | 483-511 |
| D | EnvG-CTR * | 1-17 VSV | 30-700 | 486-511 |
| E | EnvG-TM | 1-17 VSV | 30-674 | 463-511 |
| F | EnvG-SS | 1-17 | 30-650 | 446-511 |
| G | EnvG-LS | 1-17 | 30-650 | 426-511 |
| H | EnvG-XLS | 1-17 | 30-650 | 395-511 |

HIV-1 Env (Subtype A, strain BG505) Gene Insert Design for VSV. A synthetic gene sequence encoding HIV-1 Env (subtype A, strain BG505) was designed for VSV vectors as described above with some modifications.

Nucleotide sequence design:
1. The Optimizer webtool (Nucleic Acids Res 35:W126-131) was used to generate a new BG505 Env coding sequence that has a codon bias similar to VSV.
2. Homopolymer sequences >5 nucleotides (CCCCC, GGGGG) were interrupted by substitution of at least one synonymous codon.
3. Homopolymer sequences >4 nculeotides (AAAA, TTTT) were interrupted by substitution with at least one synonymous codon.
4. The 5' end of the coding sequences was modified to include a Kozak translation initiation sequence (ag-gaGCCACCATG (SEQ ID NO: 1)) (J Biol Chem 266:19867-19870)
5. An optimal translation termination signal TAAag was added to the 3' end of the coding sequences (FEBS letters 440:351-355)
6. RNA instability elements similar to UUAUUUAUU (Mol Cell Biol 15:2219-2230) were interrupted by replacing sequence with synonymous codons.
7. Potential polyadenylation signals (AAUAAA) (MMBR 63:405-445) were interrupted by substitution with synonymous codons.
8. Potential T7 polymerase terminators were removed: cTGAg, gacTAAag, ctTAAac and gacTAAat to prevent inhibition of recombinant VSV rescue from cloned DNA (Journal of molecular biology 238:145-158)
9. The mRNA splice site prediction tool NNSPLICE webtool (J Comput Biol 4:311-323) was used to predict the potential splice sites and synonymous codons were substituted.
10. A NheI(GCTAGC) site was added to the 3' end of VSV-G signal peptide
11. 5' end was modified to include a BstBI site for cloning into the rVSV genomic cDNA.
12. 3' end was modified to include a PacI site for cloning into the rVSV genomic cDNA A synthetic HIV Env gene (subtype B, strain JR-FL) was designed for incorporation into VSV vectors using the steps described in 2.2.1 with some modification. The EnvG hybrid was designed specifically for making stable VSV vectors that coexpress VSV G and Env.
1. The Optimizer webtool (Nucleic Acids Res 35:W126-131) was used to generate a new strain JR-FL Env coding sequence that has a codon bias similar to VSV.
2. Homopolymer sequences >5 nucleotides (CCCCC, GGGGG) were interrupted by substitution of at least one synonymous codon.
3. Homopolymer sequences >4 nucleotides (AAAA, TTTT) were interrupted by substitution with at least one synonymous codon.
4. The 5' end of the coding sequences was modified to include a Kozak translation initiation sequence (ag-gaGCCACCATG (SEQ ID NO: 1)) (J Biol Chem 266:19867-19870)
5. An optimal translation termination signal TGAg was added to the 3' end of the coding sequences (FEBS letters 440:351-355)
6. RNA instability elements similar to UUAUUUAUU (Mol Cell Biol 15:2219-2230) were interrupted by replacing sequence with synonymous codons.
7. Potential polyadenylation signals (AAUAAA) (MMBR 63:405-445) were interrupted by substitution with synonymous codons.
8. Potential T7 polymerase terminators were removed: cTGAg, gacTAAag, ctTAAac and gacTAAat to prevent inhibition of recombinant VSV rescue from cloned DNA (Journal of molecular biology 238:145-158)
9. The mRNA splice site prediction tool NNSPLICE webtool (J Comput Biol 4:311-323) was used to predict the potential splice sites and synonymous codons were substituted.
10. 5' end was modified to include a BstBI site for cloning into the rVSV genomic cDNA.
11. 3' end was modified to include a PacI site for cloning into the rVSV genomic cDNA In this example, an EnvG hybrid was designed with the cellular CD5 signal peptide and the VSV G transmembrane and cytoplasmic domains. Additionally, an Alanine residue was added at the C-terminus of the signal peptide to improve agreement with signal peptidase cleavage signals (Nature methods 8:785-786).

It is important to note that Applicants' gene insert optimization approach is not restricted to VSV vectors and the strategy can be modified for use across multiple vector platforms. Examples of Env gene inserts designed for expression from canine distemper virus (CDV) vectors are provided below. Env gene inserts with nucleotide sequence resembling the CDV genome can be produced and functional domains from the CDV fusion (F) protein can be functionally substituted into Env as described above for VSV G.

The gene optimization procedure also is not limited to Env immunogens. Changes to nucleotide sequence to reflect the base composition of the viral vector genome can improve the stability of other inserts. In addition, vector stability can be improved by altering specific protein signals that modulate export, posttranslational modification, or cellular localization. Examples below include an HIV gag gene insert designed for expression from VSV, SIV Gag and Env genes designed for expression by CDV, and SIV Gag and Env genes designed for expression from VSV, and a fusion protein called the HIVCON designed for expression by CDV.

Finally, Applicants have found that gene insert designed as described above also can be used in plasmid DNA expression vectors. For example, genes designed for VSV also expressed efficiently from plasmid DNA vectors. This result indicates that elements of the gene design approach Applicants have developed have more broad applicability.

Synthetic genes encoding HIV Env were designed for expression from a vector developed from an attenuated strain of canine distemper virus (CDV). Vectors expressing HIV Env subtype A (BG505) and subtype C (16055) Env have been isolated.

A synthetic HIV Env gene (subtype A, BG505) was designed for incorporation into CDV vectors steps similar to those described above with modifications. Importantly, the synthetic gene was designed using a codon bias characteristic of the CDV genome.

The gene was designed using the following steps:
1. The Optimizer Web Tool (Nucleic Acids Res 35:W126-131) was used to generate a synthetic Env gene with a nucleotide content similar to the CDV genome. CDV codon bias was retrieved from database (25).
2. Homopolymer sequences >5 nucleotides were interrupted by substitution of at least one synonymous codon.
3. The 5' end of the coding sequences was modified to include a Kozak translation initiation sequence (aggaGCCACCATG (SEQ ID NO: 1)) (J Biol Chem 266:19867-19870)
4. RNA instability elements similar to UUAUUUAUU (Mol Cell Biol 15:2219-2230) were interrupted by replacing sequence with synonymous codons.
5. Potential polyadenylation signals (AAUAAA) (MMBR 63:405-445) were interrupted by substitution with synonymous codons.
6. Potential T7 polymerase terminators were removed to prevent inhibition of recombinant CDV rescue from cloned DNA (Journal of molecular biology 238:145-158).
7. The mRNA splice site prediction webtool NNSPLICE (J Comput Biol 4:311-323) was used to predict the potential splice sites and synonymous codons were substituted.
8. Adjust insert length to ensure that introduction into the CDV genome would follow the 'Rule-of-Six" (i.e. total CDV genome length is multiples of 6) (J Virol 72:891-899).

Protein domain modifications: In this example, the Env genes were designed to encode a truncated Env proteins that lack the cytoplasmic tail. Nucleotide sequence design: An SIV (strain SIVmac239) Env gene was designed for expression by VSV vectors. As described below:
1. Replace the SIV signal sequence with VSV signal sequence, keeping the first amino acid after cleavage on SIV Env.
2. Replace the SIV Env cytoplasmic tail with VSV G.
3. The Optimizer Web Tool (Nucleic Acids Res 35:W126-131) was used to generate synthetic coding sequence with a codon bias similar to VSV based on the codon usage for Vesicular Stomatitis Indiana Virus (Nucleic Acids Res 28:292).
4. Most homopolymer stretches ≥4 nucleotides were interrupted by substitution of one or more synonymous codon(s), using the VSV codon usage table to maintain codon bias similar to VSV.
5. The 5' end of the coding sequences was modified to include a Kozak translation initiation sequence (aggaGCCACCATG(SEQ ID NO: 1)) (J Biol Chem 266:19867-19870)
6. An optimal translation termination signal TAAag was added to the 3' end of the coding sequences (FEBS letters 440:351-355)
7. The mRNA splice site prediction webtool NNSPLICE (J Comput Biol 4:311-323) was used to predict the potential splice sites, which were substituted with synonymous codons.
8. RNA instability elements similar to UUAUUUAUU (Mol Cell Biol 15:2219-2230) were interrupted by replacing sequence with synonymous codons.
9. Potential polyadenylation signals (AAUAAA) (MMBR 63:405-445) were interrupted by substitution with synonymous codons.
10. Potential T7 polymerase terminators were removed: cTGAg, gacTAAag, ctTAAac and gacTAAat to prevent inhibition of recombinant VSV rescue from cloned DNA (21)
11. 5' end includes a BstBI site and the 3' end includes a PacI site for cloning into the rVSV genomic cDNA in place of VSV G.

The C-terminal cytoplasmic domain was removed from SIV Env.

The HIVCON is an HIV immunogen designed by Letourneau et al (PLoS ONE 2:e984). The immunogen is a fusion protein composed of relatively short, highly conserved sequence elements from the HIV proteome, which is intended to elicit cellular immunity against targets that cannot be easily mutated by the virus. The HIVCON insert designed by Hanke et al was designed specifically for expression by plasmid DNA and DNA virus vectors. Applicants have made several new gene inserts designed for incorporation into canine distemper virus (CDV) vectors, which have a small negative-sense, single-stranded RNA genome.

To design a gene that was more compatible with a CDV vector, a synthetic HIVCON coding sequence (corresponding to FIG. 8C) was prepared using the following steps:
1. The optimizer Web Tool (Nucleic Acids Res 35:W126-131) was used to generate an HIVCON coding sequence that has a codon bias similar to CDV based on the Codon Usage for Canine Distemper Virus (Nucleic Acids Res 28:292).
2. All homopolymer stretches ≥4-5 nucleotides were interrupted using an alternative codon from the CDV codon usage table to maintain codon bias similar to CDV.
3. All sequences that resemble morbillivirus transcription stop or start signals (J Virol 75:921-933, Virology 193:66-72) were interrupted using an alternative codon from the CDV codon usage table.
4. Potential RNA splicing signals were identified using the webtool NNSPLICE (J Comput Biol 4:311-323) and subsequently interrupted by substitution with synonymous codons
5. RNA instability elements similar to 5-UUAUUUAUU-3' (Mol Cell Biol 15:2219-2230) were interrupted by silent mutation using an alternative codon from the CDV codon usage table to maintain codon bias similar to CDV.
6. Two sequences resembling T7 RNA polymerase terminators were interrupted using synonymous codons (Journal of molecular biology 238:145-158).
7. A Kozak sequence GGAGCCACC was inserted to improve translation (Gene 234:187-208).
8. To increase the stability of the vector and the integrity of the insert, a 2A-like peptide motif from Thosea asigna virus (EGRGSLLTCGDVEENPGP(SEQ ID NO: 2)) (J Gen Virol 89:1036-1042) was added to fuse HIVCON coding sequence with the with CDV (M) gene.
9. Coding sequence for the VSV G leader (MKCLLYLAFL-FIGVNCK (SEQ ID NO: 3)) was also incorporated at the N-terminus to promote secretion of the polypeptide immunogen.

Protein modifications: The VSV signal peptide was added to the N-terminus. At the C-terminus, a 2A-like polypeptide cleavage signal (J Gen Virol 89:1036-1042) was added between the HIVCON and matrix coding sequences. This creates a polycistronic HIVCON-Matrix gene that encodes two polypeptides as depicted in FIG. 9.

To demonstrate that genes designed by Applicants' approach were not restricted to use in RNA virus vectors like CDV and VSV, Applicants developed plasmid vectors encoding the hybrid the EnvG protein described earlier (Clade A). In addition, using the basic approach described above, Applicants also designed hybrid Env proteins (EnvF) in which domains of Env were replaced with sequences from the CDV fusion (F) protein. EnvG and EnvF genes were cloned into plasmid DNA vectors under the control of the under the control of the cytomegalovirus promoter and enhancer. Flow cytometry (EnvG) or Western blotting (EnvF) was used to evaluate transient expression of Env protein.

Figures 10A, 10B:
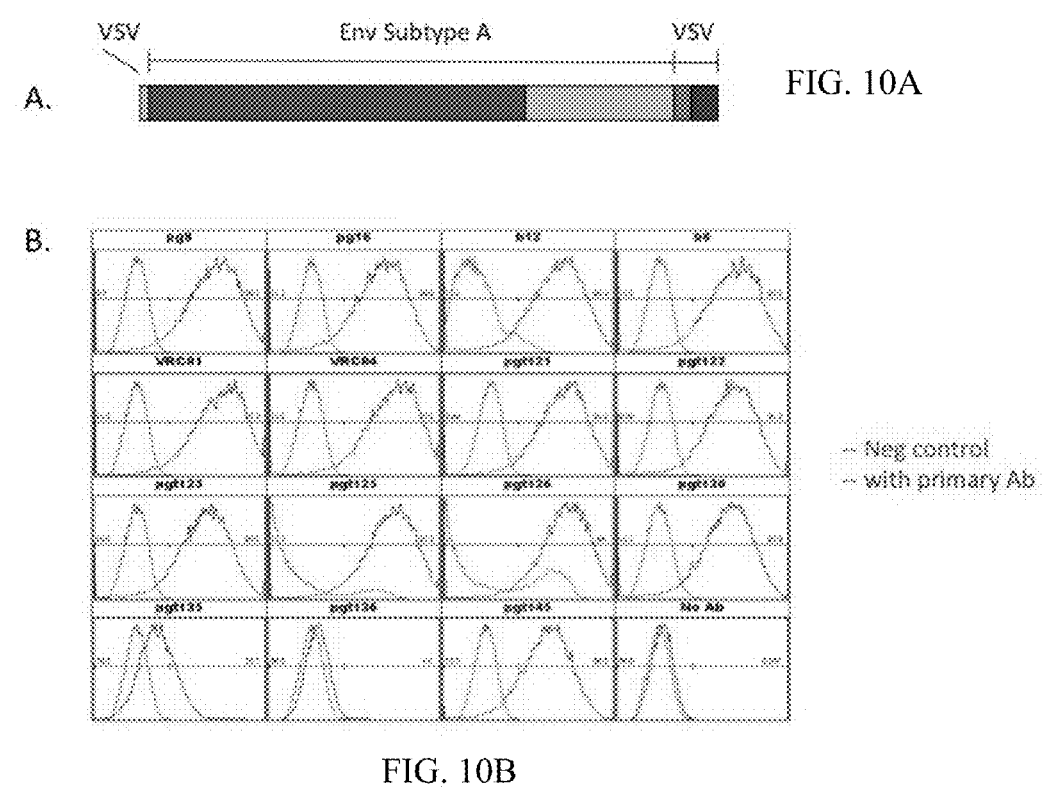

Plasmid DNA containing the EnvG (subtype A) described above was transfected into 293T cells. Cell surface expression of the EnvG proteins and its antigenic profile are illustrated in the cell sorting analysis shown in FIG. 10.

Figure 12:
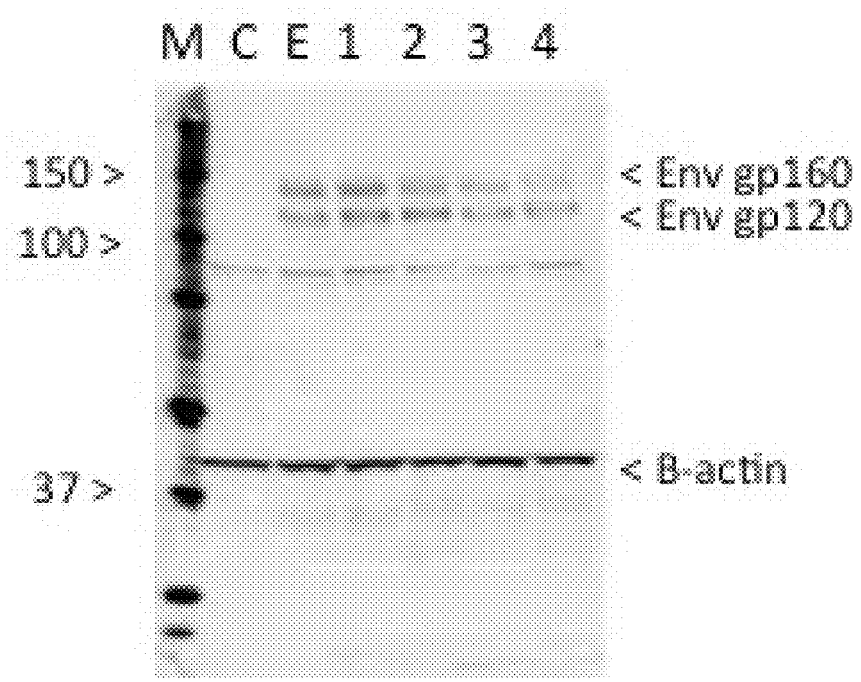
FIG. 12 depicts transient expression of EnvF in transfected 293T cells. Total cell lysates were prepared and analyzed by denaturing SDS polyacrylamide gel electrophoresis. Proteins were transferred to a membrane and reacted with anti-HIV immunoglobulin. Antibody specific for beta-actin was used as a control. M) Marker; C) untransfected control cell lysate; E) plasmid DNA containing the native unmodified Env gene; 1-4) EnvF hybrid proteins illustrated in FIG. 11.

Western blot analysis demonstrated that all four constructs were expressed from transfected plasmids (FIG. 12). The four EnvF fusion protein also were analyzed to determine whether they retained fusion function of the natural HIV Env protein. EnvF2 and EnvF4 were positive for cell membrane fusion indicating that the domain substitutions did not abolish this function (data not shown). All four EnvF proteins were positive for binding to monoclonal antibodies PG9, PG16, B6, B12, and VRC01 when expressed on the cell surface following transient expression.

The nucleotide sequences and vectors of the invention can be delivered to cells, for example if the aim is generate a viral particles containing the desired antigenic protein. Suitable transfection, transformation, or gene delivery methods can be used as part of this objective. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Generation of the viral particles containing the desired antigens can be carried out in any suitable type of host cells, such as bacterial cells, yeast, insect cells, and mammalian cells. The antigens of the invention can also be expressed including using in vitro transcription/translation systems. All of such methods are well known by those skilled in the art, and one of skill in the art would readily be able to select a suitable method depending on the nature of the nucleotide sequences, vectors, and cell types used.

The viral particles may be treated with formalin, glutaraldehyde, or other chemicals that limit viral replication. The viral particles may be treated with physical methods such as radiation, heat or adsorption onto surfaces with the result that viral replication is impaired. A virus inactivation regimen that preserves maximal antigenicity of Env is desirable. For example, VSV particles containing EnvG described in herein, can be used to make an inactivated VSV (iVSV-Env) particle for use as a vaccine immunogen. The inactivation kinetics of three known virus inactivating agents, including formalin, beta propiolactone (BPL), and ultraviolet (UV) light may be determined. Inactivation may be assessed by measuring plaque-forming units (pfu) over time.

Antigenicity of the Env spike may be assessed using a panel of well-characterized neutralizing antibodies directed at sites of vulnerability on the HIV Env spike including but not necessarily limited to the: CD4 binding site (CD4bs), mper epitopes recognized by 2F5 and 4E10 bNAbs, V1/V2 quaternary epitopes (QNE) recognized by PG9, PG16, CHO1 and Glycan-binding bNAbs recognized by PGT bNAbs (PGT121, PGT125, PGT128, PGT130).

The live or inactivated viral particles may be combined with adjuvants including, but not limited to, aluminum phosphate, aluminum hydroxide, iscoms (e.g. IscoMatrix), monphosphoryl lipid A, CpG-containing oligonucleotides, Adjuplex, cytokines (e.g. IL12), alone or in combination. The immunogenicity of an adjuvanted live or iVSV-Env for the induction of functional immune responses in experimental animals may be determined.

The optimal dose and immunization regimen for induction of Env-specific antibody response using adjuvants including aluminum phosphate and ISCOMATRIX® may be determined in animals, such as rabbits. The induction of neutralizing antibody responses using a panel of tier 1 and tier 2 viruses representing clades A, B and C may be assessed. In non-human primates, dose-ranging studies may be performed to determine the optimal vaccination regimen for iVSV chimeras. ELISA and competition-binding assays may be utilized to determine the breadth of response to the 4 major sites of vulnerability on HIV. The induction of neutralizing antibody responses may be assessed by using a panel of tier 1 and tier 2 viruses representing clades A, B and C.

Pre-GMP cell lines and virus seed stocks may be produced for generation of vaccines for clinical trials. Furthermore, pre-GMP Vero cell line that stably expresses CD4 and CCR5 may be developed. Pre-master seed stocks of VSV chimeras expressing functional Glade A, B and C envelope trimers may be developed and characterized.

In preferred embodiments, the nucleotide sequences, antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS.

The compositions of the invention may be injectable suspensions, solutions, sprays, lyophilized powders, syrups, elixirs and the like. Any suitable form of composition may be used. To prepare such a composition, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide—(e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from Mycobacterium tuberculosis, substances found in Cornyebacterium parvum, Bordetella pertussis, or members of the genus Brucella), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of infection, such as HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery may also be accomplished via a mucosal surface such as the anal, vaginal or oral mucosa. Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-VSV boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen can also include VSV vectors that derive their G protein or G/Stem protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December;74(23):10903-10). The VSV vectors used in these examples contain a G or G/Stem protein derived from the Indiana serotype of VSV. Vectors can also be constructed to express G or G/Stem molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus a prime may be delivered in the context of a G or G/Stem moelcule that is from the Indiana serotype and the immune system can be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an VSV vector containing RNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA. HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Introduction

Problems encountered frequently during vaccine delivery vector development include poor foreign protein expression, inefficient or incomplete post-translational processing of the immunogen, diminished vector propagation, and gene insert instability. These problems are often related to the foreign gene being nonessential for vector propagation and the negative effect on replicative fitness that often is conferred by the biological or physical characteristics of the nucleotide sequence or the encoded protein. To reduce the negative selective pressure caused by insertion of a foreign gene sequence while also maintaining abundant protein expression needed to develop an immunogenic vaccine, Applicants have developed a new strategy for designing protein-coding sequences for use in vaccine vectors. In summary, the objective of the method is to develop a gene insert that is more compatible with the host vector by 1) modifying the protein sequence to lessen potential interference with vector propagation while ensuring that the polypeptide is expressed and processed efficiently and maintains desired structural features, and 2) designing the gene with a nucleotide sequence that resembles the base composition of the host vector genome.

Earlier 'gene optimization' procedures used to develop gene inserts for vaccine vectors focused primarily on designing synthetic coding sequences with the characteristics of highly expressed cellular mRNAs (1, 2, 5, 10). Although this general optimization approach often increases expression of the encoded polypeptide, it also can result in a gene insert that is poorly compatible with the vector because the expressed protein is cytotoxic and/or the engineered nucleotide sequence is difficult to replicate and unstable. Accordingly, Applicants' objective is to develop a gene design approach that makes it possible to abundantly express foreign proteins while also reducing the negative effect caused by introducing foreign gene sequences into a vector genetic background. Applicants' gene optimization approach incorporates three elements:

4. The synthetic gene is designed with a codon bias similar to the vector sequence
5. Nucleotide sequence elements in the synthetic gene that resemble known 'hot spots' for mutation, inhibitors of replication or gene expression, or have the potential to direct inappropriate RNA processing are interrupted using synonymous codons.
6. Protein functional domains that modulate translation, post-translational processing, and cellular compartmentalization can be replaced with analogous operable elements from other polypeptides to produce an immunogen that is expressed abundantly while having less negative effect on vector propagation and fitness.

Below, Applicants' gene design approach is illustrated with HIV Env genes designed specifically for expression by live vesicular stomatitis virus (VSV) vectors. Other examples follow to show that the strategy is not limited to VSV vectors or Env immunogens.

Example 2

Env Gene Inserts Designed for VSV Vectors

Objective of Env Immunogen Design. An HIV vaccine that elicits durable humoral immunity, which includes antibodies that neutralize a broad spectrum of HIV isolates, will decrease the rate of infection significantly. Recent studies have shown that potent virus-neutralizing antibodies active against a wide range of HIV strains do emerge in about 10-20% of infected patients clearly demonstrating that the human immune system can produce the requisite immunoglobulins (6, 19, 31, 34). These HIV-neutralizing antibodies are specific for the viral envelope glycoprotein (Env), which is the viral protein that directs cell attachment and entry.

Antibodies that will neutralize a significant range of HIV strains have been elicited only in response to HIV infection (6, 19, 31, 34). In contrast, immune responses elicited by numerous experimental Env vaccines tested in humans and animals have evoked antibodies that were unable to neutralize virus or were active against only a very limited range of HIV strains (8). Taken together, these findings indicate that Env structures found on HIV particles and infected cells can elicit virus-neutralizing antibodies, whereas candidate vaccines have failed to duplicate or mimic the appropriate Env immunogens needed to evoke efficacious humoral immunity. Moreover, this line of reasoning predicts that the immune system must be stimulated with authentic Env structures to elicit antibodies with both Env specificity and virus neutralizing activity.

Development of a vaccine that will expose the immune system to a properly configured Env immunogen that is nearly identical to the functional structures found on the surface of HIV particles is a difficult technical problem, because the active form of Env is a membrane-bound, unstable, multi-subunit complex. Functional Env protein is part of trimeric glycoprotein spike that is assembled from subunits derived from a virus-encoded precursor protein (gp160) (7). Maturation of gp160 involves extensive post-translational modification including glycosylation, formation of multiple intra-chain disulfide linkages, and proteolytic cleavage into two subunits, which include the smaller transmembrane glycoprotein gp41 and the soluble extracellular subunit gp120. Subunits gp41 and gp120 are held together by noncovalent interactions to form a monomer and three Env monomers associate into a complex to form the functional trimeric spikes found on surface of the HIV particles and infected cells. Design and production of a vaccine that can deliver natively configured trimeric spike immunogens must take into account: 1) synthesis of immunogens that are modified extensively and correctly; 2) assembly of a stable multisubunit complex held together by labile noncovalent interactions; 3) known insolubility of the native gp41 subunit; and 4) the native spike complex is naturally anchored to the lipid bilayer of cells and virus particles. These biochemical features make it difficult to produce a soluble protein immunogen that accurately mimics a trimeric spike; thus, a vector platform that will direct synthesis of the native Env spike following vaccine administration is a more practical approach.

Development of a vector that will produce abundant trimeric Env immunogen after vaccine administration also is technically challenging. This is due to the fact that vectors encoding a full-length Env polypeptide tend to be genetically unstable and often express the protein poorly. This attributed to multiple factors including inhibitory elements in HIV nucleotide sequences (32), features of the protein that inhibit efficient translation and post-translational processing (11, 18, 37, 39, 40), and the inherent cytotoxicity caused by expression of this transmembrane glycoprotein. Nucleotide sequence "optimization" methods and a variety of protein modifications also have been tested with varying degrees of success including exchange of secretion signals, removal of glycosylation signals, substitution of transmembrane domains, or deletion or replacement of cytoplasmic domain of gp41 (11, 18, 22, 37, 39, 40).

The methods used before to improve Env expression are not applicable to all vectors and immunogen designs. For example, protein modifications introduced to improve expression might alter structural conformation producing unpredictable effects on important epitopes. Nucleotide sequence optimization also can have unpredictable effects. Notably, common gene optimization procedures generally use a codon bias reflecting highly expressed mammalian mRNAs, which may not be compatible with viral vectors that have genomes with much different nucleotide compositions. This can be illustrated with the HIV Env gene. Using online web tools (28, 30) to design an Env gene with a codon bias reflecting highly expressed mammalian genes (13, 41) results in a coding sequence that has a guanine plus cytosine (G+C) content of approximately 60%. Gene inserts with high G+C content like this might be poorly expressed or unstable when inserted into vectors like those based on RNA viruses such as measles virus, bovine parainfluenza virus, and vesicular stomatitis virus, which have noticeably lower genomic G+C content of 47%, 36%, and 42%, respectively.

Applicants' goal is to make genetically stable vaccine vectors that abundantly express trimeric membrane-bound Env spikes that closely mimic the structural properties of the functional glycoprotein complex found on HIV particles. To achieve this objective, Applicants have developed a strategy to design gene inserts that are tailored to the vector. To ensure that the modified Env immunogens encoded by Applicants' vectors are processed accurately and retain a native configuration, Applicants have developed a method to confirm the presence of different classes of epitopes known to bind with virus-neutralizing antibodies (FIG. 1). In cells expressing the Env immunogens, FACS analysis is used with antibody probes including monoclonal antibodies that recognize the CD4 binding site (VRC01 and b12) (4, 12, 38), determinant formed by the V1/V2 loops (PG9 and PG16) (36), structures formed by the glycosylated sequences in the V3 loop (PGT121, PGT126, PGT128, and PGT130) (35), the membrane-proximal external region (2F5 and 4E10) (24, 46), and unique structures formed specifically by the trimeric spike (PGT145) (35). The presence of epitopes is detected on the cell surface by FACs to confirm that the vector is directing expression of a correctly processed and assembled Env spike.

Gene Insert Optimization Method Applied to HIV Env. The foreign gene insert optimization strategy Applicants have developed is illustrated below using HIV Env (strain JR-FL, subtype B). Adaptation of this method to other types of gene inserts and vectors is included below: EnvF fusions proteins for canine distemper virus (CDV) vectors; SIV genes for CDV; SIV genes for VSV; HIV Gag for VSV; HIVCON for CDV.

In summary, the major elements of the Env gene insert optimization strategy are:

5. Design of the Env gene insert using a nucleotide bias characteristic of the VSV genome
6. Removal of RNA sequence elements that might cause VSV genome instability, inhibit protein translation, reduce mRNA stability, or promote unwanted RNA processing.
7. Addition of cis-acting RNA sequences that promote efficient translation.
8. Design of a hybrid Env immunogen in which select Env functional domains are substituted with sequences from the VSV glycoprotein (G) to promote improved protein expression. Domains from G found to improve expression while retaining Env structures recognized by neutralizing antibodies include: a) the VSV G signal sequence (secretory signal); b) the membrane proximal extracellular stem domain; c) the transmembrane domain; and/or the intracellular cytoplasmic domain. It is important to note that in some instances, replacement of Env domains with sequences from G was not beneficial. For example, the VSV signal sequence did not enhance expression or genetic stability in some VSV vectors, but further investigation revealed that substitution of the signal sequence from the cellular CD5 protein was beneficial. Thus, the domain swap strategy is generally applicable, but requires some empirical determination to achieve the greatest benefit.

HIV-1 Env (Subtype B, strain JR-FL) Gene Insert Design for VSV. Design of HIV-1 Env (subtype B, strain JR-FL) gene inserts for expression from VSV vectors.

Nucleotide sequence design:
8. The Optimizer Web Tool (28) was used to generate a new Env coding sequence with a codon bias similar to VSV.
9. The computer-generated sequence was then scanned for sequences that might have a negative effect on RNA transcription or stability, translation, or VSV genome replication. These sequences were removed by replacing nucleotides in the synthetic Env coding sequence with synonymous codons. Sequences targeted for substitution included:
   f. Most homopolymer stretches nucleotides
   g. Sequences resembling cellular mRNA splicing signals identified using NNSPLICE webtool (29)
   h. Sequences resembling known RNA instability elements (43)
   i. Sequences resembling the known cleavage and polyadenylation signal (AAUAAA) (42)
   j. Sequences resembling transcription start and stop signal consensus for VSV (3)
10. The 5' end of the coding sequences was modified to include a translation initiation context resembling a consensus for the other VSV genes (GTCATCATG)
11. Stop codon context was modified to resemble highly-expressed human genes according to Kochetov (13)
12. 5' end includes a HindIII site for cloning into the rVSV genomic cDNA.
13. For molecular cloning purposes, two sequences were edited to remove HindIII sites in the coding sequence.
14. 3' end was modified by addition of a BamHI site for cloning into the rVSV genomic cDNA Protein Modifications. Multiple domain swaps (FIG. 2) have been tested identifying several that 1) improve Env expression; 2) retain functional properties of native Env; and 3) preserve critical structural determinants recognized by neutralizing antibodies.

TABLE 1

Amino acid coordinates for sequences of HIV Env and VSV G incorporated into EnvG hybrids illustrated in FIG. 2.

| Protein | Name | N-Terminal Signal Peptide | Env (JR-FL) | VSV G |
| --- | --- | --- | --- | --- |
| A | VSV G | 1-17 VSV G | None | 18-511 |
| B | Env (JR-FL) | 1-29 Env | 30-847 | None |
| C | EnvG-CT | 1-17 VSV | 30-695 | 483-511 |
| D | EnvG-CTR * | 1-17 VSV | 30-700 | 486-511 |
| E | EnvG-TM | 1-17 VSV | 30-674 | 463-511 |
| F | EnvG-SS | 1-17 | 30-650 | 446-511 |
| G | EnvG-LS | 1-17 | 30-650 | 426-511 |
| H | EnvG-XLS | 1-17 | 30-650 | 395-511 |

HIV-1 Env (Subtype A, strain BG505) Gene Insert Design for VSV. A synthetic gene sequence encoding HIV-1 Env (subtype A, strain BG505) was designed for VSV vectors as described above with some modifications.

Nucleotide sequence design:
13. The Optimizer webtool (28) was used to generate a new BG505 Env coding sequence that has a codon bias similar to VSV.
14. Homopolymer sequences >5 nucleotides (CCCCC, GGGGG) were interrupted by substitution of at least one synonymous codon.
15. Homopolymer sequences >4 nculeotides (AAAA, TTTT) were interrupted by substitution with at least one synonymous codon.
16. The 5' end of the coding sequences was modified to include a Kozak translation initiation sequence (ag-gaGCCACCATG (SEQ ID NO: 1)) (16)
17. An optimal translation termination signal TAAag was added to the 3' end of the coding sequences (13)
18. RNA instability elements similar to UUAUUUAUU (43) were interrupted by replacing sequence with synonymous codons.
19. Potential polyadenylation signals (AAUAAA) (42) were interrupted by substitution with synonymous codons.
20. Potential T7 polymerase terminators were removed: cTGAg, gacTAAag, ctTAAac and gacTAAat to prevent inhibition of recombinant VSV rescue from cloned DNA (21)
21. The mRNA splice site prediction tool NNSPLICE webtool (29) was used to predict the potential splice sites and synonymous codons were substituted.
22. A NheI(GCTAGC) site was added to the 3' end of VSV-G signal peptide
23. 5' end was modified to include a BstBI site for cloning into the rVSV genomic cDNA.
24. 3' end was modified to include a PacI site for cloning into the rVSV genomic cDNA Protein modifications: In this example, an EnvG hybrid was designed with the VSV G signal peptide, transmembrane and cytoplasmic domains.

HIV-1 Env (Subtype C, 16055) Gene Insert Design for VSV. Nucleotide sequence design: A synthetic HIV Env gene (subtype C, strain 16055) was designed for incorporation into VSV vectors using the steps described above.

Protein domain modifications: In this example, an EnvG hybrid was designed with the cellular CD5 signal peptide and the VSV G transmembrane and cytoplasmic domains.

HIV-1 Env (Subtype B, Strain JR-FL) Gene Insert Design for VSV Enabling Stable Coexpression of Env and VSV G. Nucleotide sequence design. A synthetic HIV Env gene (subtype B, strain JR-FL) was designed for incorporation into VSV vectors using the steps described in 2.2.1 with some modification. The EnvG hybrid was designed specifically for making stable VSV vectors that coexpress VSV G and Env.

12. The Optimizer webtool (28) was used to generate a new strain JR-FL Env coding sequence that has a codon bias similar to VSV.
13. Homopolymer sequences >5 nucleotides (CCCCC, GGGGG) were interrupted by substitution of at least one synonymous codon.
14. Homopolymer sequences >4 nucleotides (AAAA, TTTT) were interrupted by substitution with at least one synonymous codon.
15. The 5' end of the coding sequences was modified to include a Kozak translation initiation sequence (ag-gaGCCACCATG (SEQ ID NO: 1)) (16)
16. An optimal translation termination signal TGAg was added to the 3' end of the coding sequences (13)

17. RNA instability elements similar to UUAUUUAUU (43) were interrupted by replacing sequence with synonymous codons.
18. Potential polyadenylation signals (AAUAAA) (42) were interrupted by substitution with synonymous codons.
19. Potential T7 polymerase terminators were removed: cTGAg, gacTAAag, ctTAAac and gacTAAat to prevent inhibition of recombinant VSV rescue from cloned DNA (21)
20. The mRNA splice site prediction tool NNSPLICE webtool (29) was used to predict the potential splice sites and synonymous codons were substituted.
21. 5' end was modified to include a BstBI site for cloning into the rVSV genomic cDNA.
22. 3' end was modified to include a PacI site for cloning into the rVSV genomic cDNA Protein domain modifications: In this example, an EnvG hybrid was designed with the cellular CD5 signal peptide and the VSV G transmembrane and cytoplasmic domains. Additionally, an Alanine residue was added at the C-terminus of the signal peptide to improve agreement with signal peptidase cleavage signals (online webtool (27)).

Figure 6:
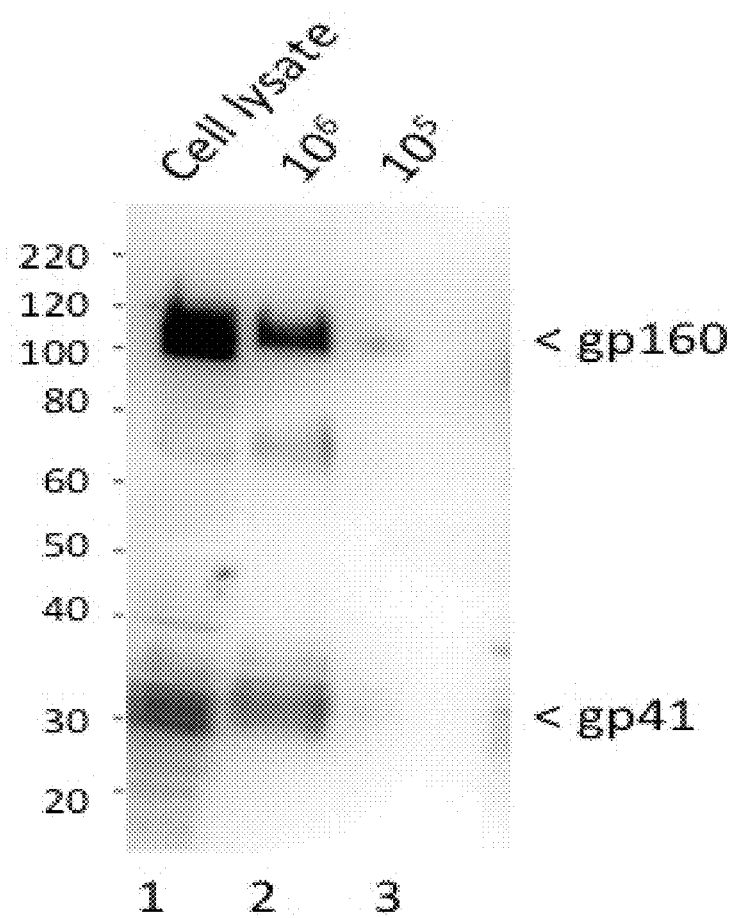
FIG. 6 depicts a Western blot analysis of EnvG proteins. Total cell lysates was prepared from Vero cells infected with the VSV vector encoding EnvG (JR-FL). The cell lysate was subjected to denaturing SDS polyacrylamide gel electrophoresis in lane 1. VSV vector particles were harvested from infected Vero cells and purified by centrifugation through a sucrose solution. $1\times10^6$ or $1\times10^5$ plaque-forming units were denatured and electrophoresed in lanes 2 and 3, respectively. The Western blot was probed with monoclonal antibody 2F5 (Muster et al., Journal of virology 67:6642-6647), which is specific for sequences present in the gp 160 precursor and the gp41 Env subunit.

Expression of the EnvG hybrid from a VSV vector is illustrated in the Western blot in FIG. 6. Infected Vero cell lysate and purified virus particles were analyzed by SDS polyacrylamide gel electrophoresis and Western blot analysis. The Western blot was probed with monoclonal antibody 2F5, which recognizes two forms of Env protein; the gp160 precursor and the gp41 subunit produced by proteolytic cleavage.

Example 3

Application of the Gene Design Strategy to Other Vectors and Gene Inserts

It is important to note that Applicants' gene insert optimization approach is not restricted to VSV vectors and the strategy can be modified for use across multiple vector platforms. Examples of Env gene inserts designed for expression from canine distemper virus (CDV) vectors are provided below. Env gene inserts with nucleotide sequence resembling the CDV genome can be produced and functional domains from the CDV fusion (F) protein can be functionally substituted into Env as described above for VSV G.

The gene optimization procedure also is not limited to Env immunogens. Changes to nucleotide sequence to reflect the base composition of the viral vector genome can improve the stability of other inserts. In addition, vector stability can be improved by altering specific protein signals that modulate export, posttranslational modification, or cellular localization. Examples below include an HIV gag gene insert designed for expression from VSV, SIV Gag and Env genes designed for expression by CDV, and SIV Gag and Env genes designed for expression from VSV, and a fusion protein called the HIVCON designed for expression by CDV.

Finally, Applicants have found that gene insert designed as described above also can be used in plasmid DNA expression vectors. For example, genes designed for VSV also expressed efficiently from plasmid DNA vectors. This result indicates that elements of the gene design approach Applicants have developed have more broad applicability.

HIV Env Gene Designs for Expression from CDV Vectors.

Synthetic genes encoding HIV Env were designed for expression from a vector developed from an attenuated strain of canine distemper virus (CDV). Vectors expressing HIV Env subtype A (BG505) and subtype C (16055) Env have been isolated. Plaques formed by infection of Vero cell monolayers are shown in FIG. 7.

Nucleotide Sequence Design:

A synthetic HIV Env gene (subtype A, BG505) was designed for incorporation into CDV vectors steps similar to those described above with modifications. Importantly, the synthetic gene was designed using a codon bias characteristic of the CDV genome.

The gene was designed using the following steps:
9. The Optimizer Web Tool (28) was used to generate a synthetic Env gene with a nucleotide content similar to the CDV genome. CDV codon preference was retrieved from database (25).
10. Homopolymer sequences >5 nucleotides were interrupted by substitution of at least one synonymous codon.
11. The 5' end of the coding sequences was modified to include a Kozak translation initiation sequence (agaGCCACCATG (SEQ ID NO: 1)) (16)
12. RNA instability elements similar to UUAUUUAUU (43) were interrupted by replacing sequence with synonymous codons.
13. Potential polyadenylation signals (AAUAAA) (42) were interrupted by substitution with synonymous codons.
14. Potential T7 polymerase terminators were removed to prevent inhibition of recombinant CDV rescue from cloned DNA (21).
15. The mRNA splice site prediction tool webtool NNSPLICE (29) was used to predict the potential splice sites and synonymous codons were substituted.
16. Adjust insert length to ensure that introduction into the CDV genome would follow the 'Rule-of-Six' (i.e. total CDV genome length is multiples of 6) (14).

Protein domain modifications: In this example, the Env genes were designed to encode a truncated Env proteins that lack the cytoplasmic tail.

SIV Env gene designed for expression from VSV. Nucleotide sequence design: An SIV (strain SIVmac239) Env gene was designed for expression by VSV vectors. As described below:
12. Replace the SIV signal sequence with VSV signal sequence, keeping the first amino acid after cleavage on SIV Env.
13. Replace the SIV Env cytoplasmic tail with VSV G.
14. The Optimizer Web Tool (28) was used to generate synthetic coding sequence with a codon bias similar to VSV based on the codon usage for Vesicular Stomatitis Indiana Virus (25).
15. Most homopolymer stretches ≥4 nucleotides were interrupted by substitution of one or more synonymous codon(s), using the VSV codon usage table to maintain codon bias similar to VSV.
16. The 5' end of the coding sequences was modified to include a Kozak translation initiation sequence (agaGCCACCATG) (16)
17. An optimal translation termination signal TAAag was added to the 3' end of the coding sequences (13)
18. The mRNA splice site prediction tool NNSPLICE webtool (29) was used to predict the potential splice sites, which were substituted with synonymous codons.

19. RNA instability elements similar to UUAUUAUU (43) were interrupted by replacing sequence with synonymous codons.
20. Potential polyadenylation signals (AAUAAA) (42) were interrupted by substitution with synonymous codons.
21. Potential T7 polymerase terminators were removed: cTGAg, gacTAAag, ctTAAac and gacTAAat to prevent inhibition of recombinant VSV rescue from cloned DNA (21)

Protein modifications: The C-terminal cytoplasmic domain was removed from SIV Env.

HIVCON Gene Design for Expression from CDV. The HIVCON is an HIV immunogen designed by Letourneau et al (17). The immunogen is a fusion protein composed of relatively short, highly conserved sequence elements from the HIV proteome, which is intended to elicit cellular immunity against targets that cannot be easily mutated by the virus. The HIVCON insert designed by Hanke et al was designed specifically for expression by plasmid DNA and DNA virus vectors. Applicants have made several new gene inserts designed for incorporation into canine distemper virus (CDV) vectors, which have a small negative-sense, single-stranded RNA genome.

To design a gene that was more compatible with a CDV vector, a synthetic HIVCON coding sequence (corresponding to FIG. 8C) was prepared using the following steps:

Nucleotide sequence design:
10. The optimizer Web Tool (28) was used to generate an HIVCON coding sequence that has a codon bias similar to CDV based on the Codon Usage for Canine Distemper Virus (25).
11. All homopolymer stretches ≥4-5 nucleotides were interrupted using an alternative codon from the CDV codon usage table to maintain codon bias similar to CDV.
12. All sequences that resemble morbillivirus transcription stop or start signals (26, 33) were interrupted using an alternative codon from the CDV codon usage table.
13. Potential RNA splicing signals were identified using the NNSPLICE webtool (29) and subsequently interrupted by substitution with synonymous codons
14. RNA instability elements similar to 5-UUAUUUAUU-3' (43) were interrupted by silent mutation using an alternative codon from the CDV codon usage table to maintain codon bias similar to CDV.
15. Two sequences resembling T7 RNA polymerase terminators were interrupted using synonymous codons (21).
16. A Kozak sequence GGAGCCACC was inserted to improve translation (15).
17. To increase the stability of the vector and the integrity of the insert, a 2A-like peptide motif from Thosea asigna virus (EGRGSLLTCGDVEENPGP (SEQ ID NO: 2)) (20) was added to fuse HIVCON coding sequence with the with CDV (M) gene.
18. Coding sequence for the VSV G leader (MKCLLY-LAFLFIGVNCK(SEQ ID NO: 3)) was also incorporated at the N-terminus to promote secretion of the polypeptide immunogen.

Protein modifications: The VSV signal peptide was added to the N-terminus. At the C-terminus, a 2A-like polypeptide cleavage signal (20) was added between the HIVCON and matrix coding sequences. This creates a polycistronic HIVCON-Matrix gene that encodes two polypeptides as depicted in FIG. 9.

Expression of EnvG and EnvF from plasmid DNA vectors. To demonstrate that genes designed by Applicants' approach were not restricted to use in RNA virus vectors like CDV and VSV, Applicants developed plasmid vectors encoding the hybrid the EnvG protein described earlier (Clade A). In addition, using the basic approach described above, Applicants also designed hybrid Env proteins (EnvF) in which domains of Env were replaced with sequences from the CDV fusion (F) protein (9). EnvG and EnvF genes were cloned into plasmid DNA vectors under the control of the under the control of the cytomegalovirus promoter and enhancer (23). Flow cytometry (EnvG) or Western blotting (EnvF) was used to evaluate transient expression of Env protein.

Transient Expression of EnvG Hybrids from Plasmid DNA.

Plasmid DNA containing the EnvG (subtype A) described above was transfected into 293T cells. Cell surface expression of the EnvG proteins and its antigenic profile are illustrated in the cell sorting analysis shown in FIG. 10.

Figure 13:
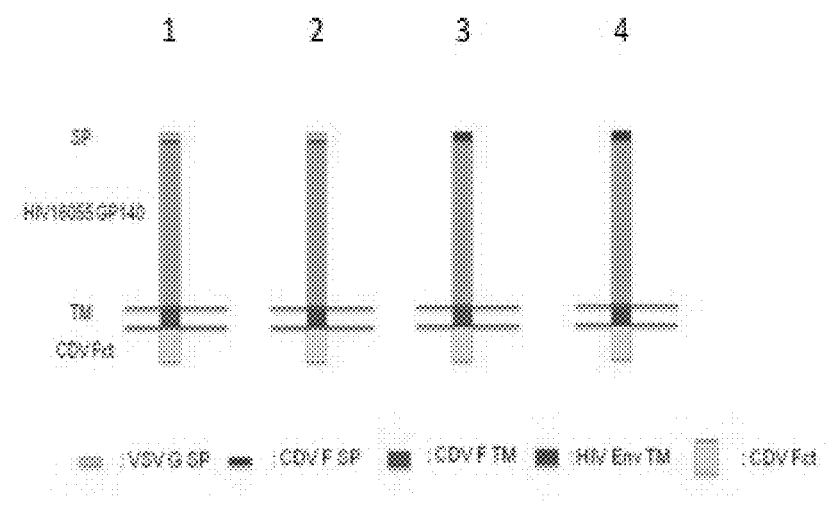

FIG. 13 depicts transient expression of EnvF hybrids from plasmid DNA.

Figure 11:
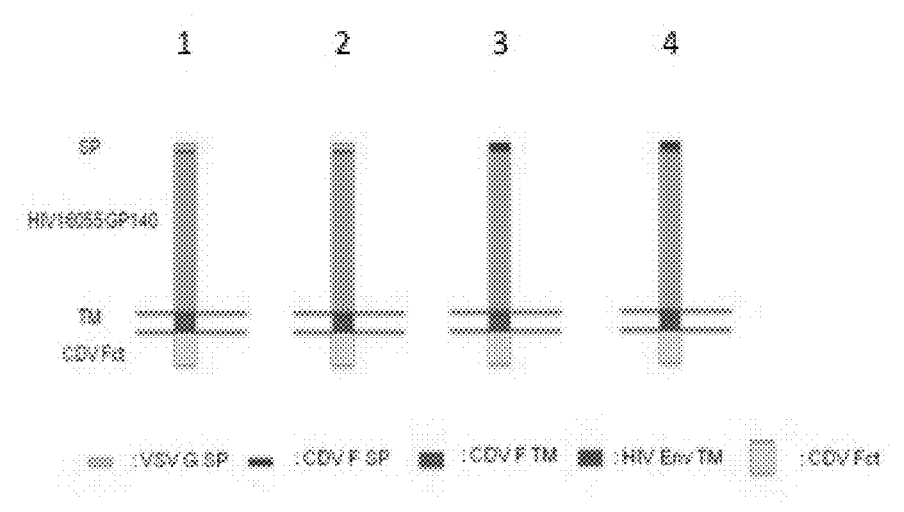

Four chimeric EnvF constructs (Subtype C, strain 16055) were designed and cloned under CMV promoter in plasmid DNA vector (FIG. 11). In addition to coding sequence design described above, F domain substitutions were made as illustrated in FIG. 11.

Expression of EnvF proteins was evaluated after transient expression in 293T cells. Western blot analysis demonstrated that all four constructs were expressed from transfected plasmids (FIG. 12). The four EnvF fusion protein also were analyzed to determine whether they retained fusion function of the natural HIV Env protein. EnvF2 and EnvF4 were positive for cell membrane fusion indicating that the domain substitutions did not abolish this function (data not shown). All four EnvF proteins were positive for binding to monoclonal antibodies PG9, PG16, B6, B12, and VRC01 when expressed on the cell surface following transient expression (data not shown).

REFERENCES

1. Andre, S., B. Seed, J. Eberle, W. Schraut, A. Bultmann, and J. Haas. 1998. Increased immune response elicited by DNA vaccination with a synthetic gp120 sequence with optimized codon usage. J Virol 72:1497-1503.
2. Barouch, D. H. 2006. Rational design of gene-based vaccines. The Journal of pathology 208:283-289.
3. Barr, J. N., S. P. Whelan, and G. W. Wertz. 2002. Transcriptional control of the RNA-dependent RNA polymerase of vesicular stomatitis virus. Biochim Biophys Acta 1577:337-353.
4. Burton, D. R., J. Pyati, R. Koduri, S. J. Sharp, G. B. Thornton, P. W. Parren, L. S. Sawyer, R. M. Hendry, N. Dunlop, P. L. Nara, and et al. 1994. Efficient neutralization of primary isolates of HIV-1 by a recombinant human monoclonal antibody. Science 266:1024-1027.
5. Donnelly, J. J., J. B. Ulmer, J. W. Shiver, and M. A. Liu. 1997. DNA vaccines. Annu Rev Immunol 15:617-648.
6. Doria-Rose, N. A., R. M. Klein, M. M. Manion, S. O'Dell, A. Phogat, B. Chakrabarti, C. W. Hallahan, S. A. Migueles, J. Wrammert, R. Ahmed, M. Nason, R. T. Wyatt, J. R. Mascola, and M. Connors. 2009. Frequency and phenotype of human immunodeficiency virus envelope-specific B cells from patients with broadly cross-neutralizing antibodies. J Virol 83:188-199.

Freed, E. O., and M. A. Martin. 2007. HIVs and thier replication, p. 2107-2186. In D. M. Knipe, D. E. Griffin, R. A. Lamb, S. E. Straus, P. M. Howley, M. A. Martin, B. Roizman, and S. E. Straus (ed.), Fields Virology. Lippincott Williams & Wilkins.

8. Girard, M. P., and W. C. Koff. 2008. Human immunodeficiency virus vaccines, p. 1213-1252. In S. A. Plotkin, W. A. Orenstein, and P. A. Offit (ed.), Vaccines, 5 ed. Elsevier, Philadelphia.

9. Griffin, D. E. 2007. Measles virus, p. 1551-1586. In D. M. Knipe, D. E. Griffin, R. A. Lamb, S. E. Straus, P. M. Howley, M. A. Martin, B. Roizman, and S. E. Straus (ed.), Fields Virology, vol. 2. Wolters Kluwer, Philadelphia.

10. Haas, J., E. C. Park, and B. Seed. 1996. Codon usage limitation in the expression of HIV-1 envelope glycoprotein. Current biology: CB 6:315-324.

11. Johnson, J. E., W. Rodgers, and J. K. Rose. 1998. A plasma membrane localization signal in the HIV-1 envelope cytoplasmic domain prevents localization at sites of vesicular stomatitis virus budding and incorporation into VSV virions. Virology 251:244-252.

12. Kessler, J. A., 2nd, P. M. McKenna, E. A. Emini, C. P. Chan, M. D. Patel, S. K. Gupta, G. E. Mark, 3rd, C. F. Barbas, 3rd, D. R. Burton, and A. J. Conley. 1997. Recombinant human monoclonal antibody IgG1b12 neutralizes diverse human immunodeficiency virus type 1 primary isolates. AIDS research and human retroviruses 13:575-582.

13. Kochetov, A. V., I. V. Ischenko, D. G. Vorobiev, A. E. Kel, V. N. Babenko, L. L. Kisselev, and N. A. Kolchanov. 1998. Eukaryotic mRNAs encoding abundant and scarce proteins are statistically dissimilar in many structural features. FEBS letters 440:351-355.

14. Kolakofsky, D., T. Pelet, D. Garcin, S. Hausmann, J. Curran, and L. Roux. 1998. Paramyxovirus RNA synthesis and the requirement for hexamer genome length: the rule of six revisited. J Virol 72:891-899.

15. Kozak, M. 1999. Initiation of translation in prokaryotes and eukaryotes. Gene 234:187-208.

16. Kozak, M. 1991. Structural features in eukaryotic mRNAs that modulate the initiation of translation. J Biol Chem 266:19867-19870.

17. Letourneau, S., E. J. Im, T. Mashishi, C. Brereton, A. Bridgeman, H. Yang, L. Dorrell, T. Dong, B. Korber, A. J. McMichael, and T. Hanke. 2007. Design and preclinical evaluation of a universal HIV-1 vaccine. PLoS ONE 2:e984.

18. Li, Y., L. Luo, D. Y. Thomas, and C. Y. Kang. 1994. Control of expression, glycosylation, and secretion of HIV-1 gp120 by homologous and heterologous signal sequences. Virology 204:266-278.

19. Li, Y., K. Svehla, M. K. Louder, D. Wycuff, S. Phogat, M. Tang, S. A. Migueles, X. Wu, A. Phogat, G. M. Shaw, M. Connors, J. Hoxie, J. R. Mascola, and R. Wyatt. 2009. Analysis of neutralization specificities in polyclonal sera derived from human immunodeficiency virus type 1-infected individuals. J Virol 83:1045-1059.

20. Luke, G. A., P. de Felipe, A. Lukashev, S. E. Kallioinen, E. A. Bruno, and M. D. Ryan. 2008. Occurrence, function and evolutionary origins of '2A-like' sequences in virus genomes. J Gen Virol 89:1036-1042.

21. Macdonald, L. E., R. K. Durbin, J. J. Dunn, and W. T. McAllister. 1994. Characterization of two types of termination signal for bacteriophage T7 RNA polymerase. Journal of molecular biology 238:145-158.

22. Megati, S., D. Garcia-Hand, S. Cappello, V. Roopchand, A. Masood, R. Xu, A. Luckay, S. Y. Chong, M. Rosati, S. Sackitey, D. B. Weiner, B. K. Felber, G. N. Pavlakis, Z. R. Israel, L. R. Smith, J. H. Eldridge, M. K. Sidhu, and M. A. Egan. 2008. Modifying the HIV-1 env gp160 gene to improve pDNA vaccine-elicited cell-mediated immune responses. Vaccine 26:5083-5094.

23. Meier, J. L., and M. F. Stinski. 1996. Regulation of human cytomegalovirus immediate-early gene expression. Intervirology 39:331-342.

24. Muster, T., F. Steindl, M. Purtscher, A. Trkola, A. Klima, G. Himmler, F. Ruker, and H. Katinger. 1993. A conserved neutralizing epitope on gp41 of human immunodeficiency virus type 1. Journal of virology 67:6642-6647.

25. Nakamura, Y., T. Gojobori, and T. Ikemura. 2000. Codon usage tabulated from international DNA sequence databases: status for the year 2000. Nucleic Acids Res 28:292.

26. Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol 75:921-933.

27. Petersen, T. N., S. Brunak, G. von Heijne, and H. Nielsen. 2011. SignalP 4.0: discriminating signal peptides from transmembrane regions. Nature methods 8:785-786.

28. Puigbo, P., E. Guzman, A. Romeu, and S. Garcia-Vallve. 2007. OPTIMIZER: a web server for optimizing the codon usage of DNA sequences. Nucleic Acids Res 35:W 126-131

29. Reese, M. G., F. H. Eeckman, D. Kulp, and D. Haussler. 1997. Improved splice site detection in Genie. J Comput Biol 4:311-323.

30. Richardson, S. M., P. W. Nunley, R. M. Yarrington, J. D. Boeke, and J. S. Bader. 2010. GeneDesign 3.0 is an updated synthetic biology toolkit. Nucleic Acids Res 38:2603-2606.

31. Sather, D. N., J. Armann, L. K. Ching, A. Mavrantoni, G. Sellhorn, Z. Caldwell, X. Yu, B. Wood, S. Self, S. Kalams, and L. Stamatatos. 2009. Factors associated with the development of cross-reactive neutralizing antibodies during human immunodeficiency virus type 1 infection. J Virol 83:757-769.

32. Schwartz, S., M. Campbell, G. Nasioulas, J. Harrison, B. K. Felber, and G. N. Pavlakis. 1992. Mutational inactivation of an inhibitory sequence in human immunodeficiency virus type 1 results in Rev-independent gag expression. J Virol 66:7176-7182.

33. Sidhu, M. S., W. Husar, S. D. Cook, P. C. Dowling, and S. A. Udem. 1993. Canine distemper terminal and intergenic non-protein coding nucleotide sequences: completion of the entire CDV genome sequence. Virology 193: 66-72.

34. Stamatatos, L., L. Morris, D. R. Burton, and J. R. Mascola. 2009. Neutralizing antibodies generated during natural HIV-1 infection: good news for an HIV-1 vaccine? Nature medicine 15:866-870.

35. Walker, L. M., M. Huber, K. J. Doores, E. Falkowska, R. Pejchal, J. P. Julien, S. K. Wang, A. Ramos, P. Y. Chan-Hui, M. Moyle, J. L. Mitcham, P. W. Hammond, 0. A. Olsen, P. Phung, S. Fling, C. H. Wong, S. Phogat, T. Wrin, M. D. Simek, W. C. Koff, I. A. Wilson, D. R. Burton, and P. Poignard. 2011. Broad neutralization coverage of HIV by multiple highly potent antibodies. Nature 477:466-470.

36. Walker, L. M., S. K. Phogat, P. Y. Chan-Hui, D. Wagner, P. Phung, J. L. Goss, T. Wrin, M. D. Simek, S. Fling, J. L. Mitcham, J. K. Lehrman, F. H. Priddy, O. A. Olsen, S. M. Frey, P. W. Hammond, S. Kaminsky, T. Zamb, M. Moyle, W. C. Koff, P. Poignard, and D. R. Burton. 2009. Broad and potent neutralizing antibodies from an African donor reveal a new HIV-1 vaccine target. Science 326:285-289.
37. Wang, B. Z., W. Liu, S. M. Kang, M. Alam, C. Huang, L. Ye, Y. Sun, Y. Li, D. L. Kothe, P. Pushko, T. Dokland, B. F. Haynes, G. Smith, B. H. Hahn, and R. W. Compans. 2007. Incorporation of high levels of chimeric human immunodeficiency virus envelope glycoproteins into virus-like particles. J Virol 81:10869-10878.
38. Wu, X., Z. Y. Yang, Y. Li, C. M. Hogerkorp, W. R. Schief, M. S. Seaman, T. Zhou, S. D. Schmidt, L. Wu, L. Xu, N. S. Longo, K. McKee, S. O'Dell, M. K. Louder, D. L. Wycuff, Y. Feng, M. Nason, N. Doria-Rose, M. Connors, P. D. Kwong, M. Roederer, R. T. Wyatt, G. J. Nabel, and J. R. Mascola. 2010. Rational design of envelope identifies broadly neutralizing human monoclonal antibodies to HIV-1. Science 329:856-861
39. Wyatt, L. S., I. M. Belyakov, P. L. Earl, J. A. Berzofsky, and B. Moss. 2008. Enhanced cell surface expression, immunogenicity and genetic stability resulting from a spontaneous truncation of HIV Env expressed by a recombinant MVA. Virology 372:260-272.
40. Wyatt, L. S., P. L. Earl, W. Xiao, J. L. Americo, C. A. Cotter, J. Vogt, and B. Moss. 2009. Elucidating and minimizing the loss by recombinant vaccinia virus of human immunodeficiency virus gene expression resulting from spontaneous mutations and positive selection. J Virol 83:7176-7184.
41. Zhang, M. Q. 1998. Statistical features of human exons and their flanking regions. Human molecular genetics 7:919-932.
42. Zhao, J., L. Hyman, and C. Moore. 1999. Formation of mRNA 3' ends in eukaryotes: mechanism, regulation, and interrelationships with other steps in mRNA synthesis. Microbiology and molecular biology reviews: MMBR 63:405-445.
43. Zubiaga, A. M., J. G. Belasco, and M. E. Greenberg. 1995. The nonamer UUAUUUAUU is the key AU-rich sequence motif that mediates mRNA degradation. Mol Cell Biol 15:2219-2230.
44. Zwick, M. B., L. L. Bonnycastle, A. Menendez, M. B. Irving, C. F. Barbas, 3rd, P. W. Parren, D. R. Burton, and J. K. Scott. 2001. Identification and characterization of a peptide that specifically binds the human, broadly neutralizing anti-human immunodeficiency virus type 1 antibody b12. J Virol 75:6692-6699.
45. Zwick, M. B., and D. R. Burton. 2007. HIV-1 neutralization: mechanisms and relevance to vaccine design. Curr HIV Res 5:608-624.
46. Zwick, M. B., A. F. Labrijn, M. Wang, C. Spenlehauer, E. O. Saphire, J. M. Binley, J. P. Moore, G. Stiegler, H. Katinger, D. R. Burton, and P. W. Parren. 2001. Broadly neutralizing antibodies targeted to the membrane-proximal external region of human immunodeficiency virus type 1 glycoprotein gp41. J Virol 75:10892-10905.

The invention is further described by the following numbered paragraphs:
1. A method for developing a gene insert compatible with a host vector comprising:
  a. modifying a protein sequence of the gene insert to lessen potential interference with vector propagation while ensuring that the protein encoded by the gene insert is expressed and processed efficiently and maintains desired structural features and
  b. designing the gene insert with a nucleotide sequence that resembles a base composition of the host vector.
2. The method of paragraph 1, wherein the gene insert is designed with a codon bias similar to the host vector.
3. The method of paragraph 1 or 2, wherein the nucleotide sequence elements in the gene insert resemble known hot spots for mutation, inhibitors of replication or gene expression or direct inappropriate RNA processing are interrupted with synonymous codons.
4. The method of any one of paragraphs 1-3, wherein the desired structural features that modulate translation, post-translational processing and cellular compartmentalization are abundantly expressed and have a less negative effect on vector propagation and fitness.
5. The method of any one of paragraphs 1-4, wherein the gene insert is HIV Env.
6. The method of paragraph 5, wherein the host vector is VSV.
7. The method of paragraph 6, wherein the Env gene insert is designed with a nucleotide bias characteristic of VSV.
8. The method of paragraph 6 or 7, wherein RNA sequence elements that might cause VSV genome instability, inhibit protein translation, reduce mRNA stability, or promote unwanted RNA processing are removed.
9. The method of any one of paragraphs 6-8, wherein cis-acting RNA sequences that promote efficient translation are added.
10. The method of any one of paragraphs 6-9, wherein the Env gene insert is substituted with sequences from VSV glycoprotein (G).
11. The method of paragraph 10 wherein the sequences from VSV G are selected from the group consisting of the VSV G signal sequence (secretory signal); the membrane proximal extracellular stem domain; the transmembrane domain; and/or the intracellular cytoplasmic domain.
12. The method of any one of paragraphs 6-11, wherein the codon bias of the Env gene insert is similar to VSV.
13. The method of paragraph 12, wherein the codon bias is changed to a sequence consisting of homopolymer stretches ≥5 nucleotides, sequences resembling cellular mRNA splicing signals, sequences resembling RNA instability elements, sequences resembling a cleavage and polyadenylation signal (AAUAAA) and sequences resembling transcription start and stop signal consensus for VSV.
14. The method of any one of paragraphs 1-5, wherein the host vector is canine distemper virus (CDV).
15. The method of paragraph 14, wherein functional domains from the CDV fusion (F) protein are substituted into Env gene insert.
16. The method of any one of paragraphs 1-4, wherein the gene insert is HIV gag, SIV gag, SIV Env, or HIVCON.
17. The method of paragraph 16, wherein the host vector is CDV, VSV or a plasmid vector.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for improving protein expression, vector propagation, and genetic stability in individual vector platforms comprising
(a) developing a gene insert compatible with a canine distemper virus (CDV) host vector comprising:
(i) modifying a protein sequence of the gene insert, wherein the protein is human immunodeficiency virus (HIV) envelope glycoprotein (Env) or HIVCON, wherein the protein encoded by the gene insert is expressed from the vector to produce a protein that maintains native structural features; and
wherein the Env or HIVCON gene insert is a hybrid that includes sequences encoding functional domains substituted with sequences encoding analogous functional domains from a CDV fusion protein (F); and
(ii) removing potential T7 polymerase terminators, and
(iii) making one or more modifications to the nucleotide sequence of the gene insert;
(b) cloning the gene insert into the CDV host vector; thereby improving protein expression, vector propagation, and genetic stability in individual vector platforms; and
(c) expressing the protein encoded by the vector in a cell.

2. The method of claim 1, wherein cis-acting RNA sequences for enhancing translation are added and wherein translation is enhanced in comparison to a vector without the sequences.

3. The method of claim 1, wherein the one or more modifications to the nucleotide sequence of the gene insert comprises
interrupting one or more homopolymer sequences >5 nucleotides CCCCC and GGGGG by substitution of at least one synonymous codon
modifying the 5' end of the coding sequences to include a Kozak translation initiation sequence having the sequence of SEQ ID NO: 1;
adding a TAAag translation termination signal to the 3' end of the coding sequences;
interrupting RNA instability elements comprising UUAUUUAUU by replacement with synonymous codons;
interrupting a potential polyadenylation signal comprising AAUAAA by substitution with synonymous codons; and/or
removing potential T7 RNA polymerase terminators cTGAg, gacTAAag, ctTAAac and gacTAAat to prevent inhibition of recombinant-CDV rescue from cloned DNA.

4. The method of claim 1 further comprising:
(d) measuring binding of the protein to antibodies specific to the native structural features of the gene insert.

5. The method of claim 1, wherein the HIV Env is Subtype A Env or Subtype C Env.

6. The method of claim 5, wherein the HIV Env is from strain BG505.

7. The method of claim 5, wherein the one or more modifications to the nucleotide sequence of a HIV Env gene further comprises
generating a synthetic Env gene with a codon optimized nucleotide content using CDV codon bias retrieved from a database;
predicting potential mRNA splice sites and substituting synonymous codons; and/or
adjusting insert length to ensure that introducing the total CDV genome length is multiples of six.

8. The method of claim 5, wherein the Subtype C Env is further modified to generating coding sequences for a hybrid Env protein containing one or more domains obtained from CDV F thereby generating an Env-F protein.

9. The method of claim 1, wherein the protein is HIV-CON.

10. The method of claim 9, wherein the one or more modifications to the nucleotide sequence of a HIVCON gene further comprises
modifying the HIVCON gene with a CDV codon bias with viral transcription start and stop signals flanking the HIVCON gene;
modifying the HIVCON gene for insertion downstream of the CDV P gene;
fusing the HIVCON coding sequence to the Matrix (M) gene of CDV to form a polycistronic coding sequence, optionally inserting a 2A-like element between the HIVCON and M coding sequence;
interrupting morbillivirus transcription stop or start signals using an alternative codon;
and/or
adding a (vesicular stomatitis virus (VSV) signal peptide to the N-terminus of the HIVCON gene.

11. The method of claim 9, wherein the nucleotide sequence encoding HIVCON comprises SEQ ID NO: 7.

* * * * *